United States Patent
Kajikawa et al.

(10) Patent No.: US 8,828,387 B2
(45) Date of Patent: Sep. 9, 2014

(54) ANTIBODY HAVING ANTI-CANCER ACTIVITY

(75) Inventors: Masunori Kajikawa, Komagane (JP); Masahito Sugiura, Komagane (JP); Kazuyuki Atarashi, Komagane (JP); Emi Shimizu, Komagane (JP); Chiemi Matsumi, Komagane (JP); Yukie Saitoh, Komagane (JP)

(73) Assignee: Actgen Inc, Nagano (JP)

( * ) Notice: Subject to any disclaimer, the term of this patent is extended or adjusted under 35 U.S.C. 154(b) by 206 days.

(21) Appl. No.: 13/382,468

(22) PCT Filed: Jul. 7, 2010

(86) PCT No.: PCT/JP2010/061526
§ 371 (c)(1),
(2), (4) Date: Jan. 5, 2012

(87) PCT Pub. No.: WO2011/004837
PCT Pub. Date: Jan. 13, 2011

(65) Prior Publication Data
US 2012/0107364 A1 May 3, 2012

(30) Foreign Application Priority Data
Jul. 8, 2009 (JP) ................................ 2009-162193

(51) Int. Cl.
A61K 39/395 (2006.01)
C07K 16/30 (2006.01)
A61K 39/00 (2006.01)

(52) U.S. Cl.
CPC ........... *C07K 16/30* (2013.01); *A61K 2039/505* (2013.01); *C07K 2317/73* (2013.01); *C07K 16/3046* (2013.01)
USPC ...................................................... 424/133.1

(58) Field of Classification Search
None
See application file for complete search history.

(56) References Cited

U.S. PATENT DOCUMENTS

2006/0294607 A1  12/2006  Fitzhugh et al.

FOREIGN PATENT DOCUMENTS

| JP | 06-011507 | 1/1994 |
| JP | 2007-014229 | 1/2007 |
| WO | WO 01/34797 A1 | 5/2001 |
| WO | WO 02/079492 A2 | 10/2002 |
| WO | WO 2004/109286 A2 | 12/2004 |
| WO | WO 2005/054459 A1 | 6/2005 |
| WO | WO 2006/113671 A2 | 10/2006 |
| WO | WO 2007/102787 A1 | 9/2007 |

OTHER PUBLICATIONS

JP Publication No. 06-011507 (abstract only) (1994).*
Brown et al (J. Immunol. May 1996; 156(9):3285-3291.*
Vajdos et al (J. Mol. Biol. Jul. 5, 2002;320(2); 415-428).*
Paul, Fundamental Immunology, 3rd Edition, 1993, pp. 292-295.*
Rudikoff et al(Proc. Natl. Acad. Sci. USA 1982 vol. 79: p. 1979).*
Pascalis et al (The Journal of Immunology (2002) 169, 3076-3084).*
Casset et al. (2003) BBRC 307, 198-205.*
English translation of International Preliminary Report on Patentability for PCT/JP2010/061526 dated Feb. 23, 2012.
Andre B. Choo, et al., "Selection Against Undifferentiated Human Embryonic Stem Cells by a Cytotoxic Antibody Recognizing Podocalyxin-Like Protein-1," Stem Cells, vol. 26, pp. 1454-1463 (2008).
Chugai-Igakusha, "Development of Hematopoietic Stem Cell: from Basic to Genetherapy," Regenerative Medicine, Ozawa Keiya editor, pp. 38-45 (2002).
David B. Kershaw, et al., "Molecular Cloning and Characterization of Human Podocalyxin-like Protein," The Journal of Biological Chemistry, vol. 272, No. 26, pp. 15708-15714 (1997).
David B. Kershaw, et al., "Molecular Cloning, Expression, and Characterization of Podocalyxin-like Protein 1 from Rabbit as a Transmembrane Protein of Glomerular Podocytes and Vascular Endothelim," The J.Biol.Chem., vol. 270, No. 49, pp. 29439-29446 (1995).
Heng Liang Tan, et al., "mAb 84, a Cytotoxic Antibody that Kills Undifferentiated Human Embryonic Stem Cells via Oncosis," Stem Cells, vol. 27, pp. 1792-1801 (2009).
International Search Report dated Aug. 31, 2010 issued during prosecution of Application No. PCT/JP2010/061526.
von Mehren et al., "Monoclonal Antibody Therapy for Cancer", Annual Review of Medicine: Selected Topics in the Clinical Sciences, Annual Reviews Inc' 54:343-369 (2003).
Database UniProt [Online] "RecName: Full=Prodocalyxin-like protein 2; AltName: Full=Endoglycan; Flags: Precursor", retrieved from EBI Accession No. UNIPROT:Q9NZ53 (Oct. 1, 2000).
Schopperle et al., "Human embryonal carcinoma tumor antigen, GP200/GCTM-2, is podocalyxin", Biochemical and Biophysical Research Communications, 300(2):285-290 (2003).
Communication for EP 10797148 dated Feb. 4, 2014, with Supplementary European Search Report dated Jan. 24, 2014.

* cited by examiner

*Primary Examiner* — Sheela J Huff
(74) *Attorney, Agent, or Firm* — Sughrue Mion, PLLC

(57) ABSTRACT

By utilizing an SST-REX method, a cDNA encoding a protein expressed on a cell surface or secreted from the cell was selected from a cDNA library derived from a cancer cell line. Monoclonal antibodies against the protein encoding the selected cDNA were prepared. The in vitro and in vivo anti-cancer activities and binding to various cancer cells lines were examined. As a result, a monoclonal antibody which binds to a PODXL2 protein, and which had excellent anti-cancer activities was found. Further, a region including an epitope of the antibody was successfully identified, and the amino acid sequences of variable regions of a light chain and a heavy chain were successfully determined.

14 Claims, 16 Drawing Sheets
(7 of 16 Drawing Sheet(s) Filed in Color)

Fig.9

LIGHT CHAIN VARIABLE REGION

MDFQVQIFSF LLISASVIIS RGQIVLTQSP AIMSASPGEK VSMTCSASSS VSYMHWYQQK

SGTSPKRWIY DTSKLASGVP ARFSGSGSGT SYSLTISSME AEDAATYYCL QWSSNPPTFG

GGTKLE

HEAVY CHAIN VARIABLE REGION

MEWSWIFLFL LSGTAGVHSE VQLQQSGPEL VKPGASVKMS CKASGYTFTS YVMHWVKQKP

GQGLEWIGYI HPYNDGIKYN EKFKGKATLT SDKSSSTAYM DLSSLTSEDS AVYYCARSWD

WYFDVWAAGT TVTVSS

———— SIGNAL SEQUENCE ----- CDR REGION

ANTIBODY HAVING ANTI-CANCER ACTIVITY

CROSS REFERENCE TO RELATED APPLICATIONS

This application is a National Stage of International Application No. PCT/JP2010/061526 filed Jul. 7, 2010, claiming priority based on Japanese Patent Application No. 2009-162193, filed Jul. 8, 2009, the contents of all of which are incorporated herein by reference in their entirety.

TECHNICAL FIELD

The present invention relates to an antibody having an anti-cancer activity and the uses thereof.

BACKGROUND ART

Cancer (tumor) is the number one cause of death in Japan. According to the statistics from the Center for Cancer Control and Information Services in independent administrative institution the National Cancer Center, Japan, the number of people who died of cancer in 2006 was approximately 329,000. On a site basis, the number for men increases in the order of lung (23%), stomach (17%), liver (11%), colon (7%, or 11% as the whole of the large intestine), and pancreas (6%), while the number for women increases in the order of stomach (13%), lung (13%), colon (10%, or 14% as the whole of the large intestine), breast (9%), and liver (8%). The number of patients is increasing year after year, and development of highly effective and safe drugs and treatment methods are strongly desired.

Gastric cancer is one of cancers which are very high in both of morbidity rate and mortality rate in Japan, but is now also considered as one of cancers which are relatively easy to cure by advancement in diagnostic methods and treatment methods mainly including chemotherapy and surgical resection through operation. However, scirrhous gastric cancer is considered as one of highly malignant gastric cancers which are difficult to treat. Scirrhous gastric cancer has the following characteristics. The cancer cells do not appear on the surface of a mucous membrane, but diffusely infiltrate the entire stomach wall or half to ⅓ or more thereof. The scirrhous gastric cancer thickens and hardens the stomach wall without forming tumoral mass which is obvious with naked eyes. Further, the boundary between the lesion and the surrounding mucous membrane is unclear. Scirrhous gastric cancer progresses faster than usual gastric cancers even if the age of onset is young, and is also difficult to diagnose. At the time when the diagnosis is made, peritoneal dissemination or metastasis has already occurred and no operation is available in 60% of the cases. Even if resection is performed by a surgery, the five-year survival rate is only 15 to 20%.

Recently, the importance of a use of an antibody as an anti-cancer agent is increasingly recognized as an approach in treating various disease conditions (of cancer types). For example, in a case of an antibody targeting a tumor-specific antigen, the antibody thus administrated is assumed to accumulate at the tumor. Accordingly, attack on cancer cells can be expected by an immune system through complement-dependent cytotoxicity (CDC) or antibody-dependent cell-mediated cytotoxicity (ADCC). Moreover, by binding an agent such as a radionuclide or cytotoxic substance to an antibody in advance, the agent thus bound can be efficiently transferred to a tumor site. Thereby, the amount of the agent reaching to the other tissues can be reduced, and consequently reduction in side effect can be expected. By administering an antibody having an agonistic activity in a case where a tumor-specific antigen has an activity to induce cell death, or by administering an antibody having a neutralizing activity in a case where a tumor-specific antigen is involved in cell growth and survival, termination or shrinkage of tumor growth can be expected from the accumulation of the tumor-specific antibody and the activity of the antibody. Because of such abilities, it is thought that an antibody is suitably applied as an anti-cancer agent.

As antibody drugs having being put on the market so far for leukemia and lymphoma, rituximab (product name rituxan) and iburitumomab tiuxetan (product name Zevalin) targeting CD20, gemtuzumab ozogamicin (product name Mylotarg) targeting CD33, and so forth have been developed. Further, for epithelial solid cancer such as breast cancer, trastuzumab (product name Herceptin) targeting Her2/neu, bevacizumab (product name Avastin) targeting VEGF, and so forth have been developed. Besides, for target diseases other than cancers, such as Rheumatoid arthritis and Castleman's disease, tocilizumab (product name Actemura) which is a human IL-6 receptor antibody, and so forth, have been developed.

However, the number of antibody drugs approved by 2008 is approximately 20 in the United States and approximately 10 in Japan. Particularly, against solid cancers, only few antibody drugs are effective. Hence, further development of effective antibody drugs is desired.

Meanwhile, "*Homo sapiens* podocalyxin-like (PODXL), transcript variant 2 (NM_005397.3)" (hereinafter, referred to as "PODXL2") is known as a type I transmembrane glycoprotein which exists in a cell membrane and which has a highly glycosylated extracellular region. The human-derived PODXL2 molecule is identified as a glycoprotein homologous molecule of a rabbit podocalyxin molecule glycosylated with a foot process of a glomerular epithelial cell (podocyte), at human glomerular foot process and endothelial cell surface (Non Patent Literatures 1, 2).

Since having an N-terminal extracellular region subjected to characteristic glycosylation, PODXL2 is classified into sialomucin family. To the family, those expressed in hematopoietic cells or hematopoietic microenvironments (vascular endothelial cell and the like), such as CD34, CD164, CD162, CD43, and Endoglycan, belong. Homologous molecules of PODXL2 have been found so far in rat, rabbit, mouse, and human. The presence of a PODXL2-like molecule is expected in other vertebrates, also. Since having a similar tissue localization, these molecules are expected to be molecules having a similar function. Nevertheless, it is known that the N-terminal amino acid sequence considered as an extracellular region is less conserved among species.

Meanwhile, Miyajima et al. have revealed the presence of a hemangioblast that is a common precursor of a blood cell and a vascular endothelial cell in an AGM region (Aorta-Gonad-Mesonephros) where adult hematopoiesis is to occur. Further, a method of isolating and culturing a hemangioblast is established, and a mouse PODXL homologous molecule (PCLP1) is identified by expression cloning using a monoclonal antibody against a surface antigen on a mouse AGM-derived cell line. When fractioned and cultured in vitro, PCLP1 positive/CD45 negative cells are differentiated into endothelial-like cells, angioblast-like cells, and hematopoietic cells. Moreover, when PCLP1 positive/CD45 negative cells are transferred into a mouse defective in a hematopoietic function, a hematopoietic system is reconstructed over a long period of time. These facts indicate that the PCLP1 positive/CD45 negative cells contain mammalian hemangioblasts capable of expressing the activity of long-term repopulating hematopoietic stem cells (LTR-HSC). It is revealed that PCLP1 functions as a marker of a hemangioblast that is a common precursor to a blood cell and a vascular endothelial cell (Patent Literatures 1, 2 and Non Patent Literature 3). In addition, by microarray analysis and the like, PCLP1 has been found as one of genes having differences in an expression before and after differentiation of a stem cell, or in foamy cell differentiation, angiogenesis, and the like (Patent Literatures 3 to 6).

As to an antibody against PODXL2, utilization thereof in separation and amplification of a hematopoietic stem cell and the like has been disclosed (Patent Literature 7). In addition, measurement using an antibody against PODXL2 as a diagnosis marker for a kidney disorder has been disclosed (Patent Literature 8). Moreover, since PODXL molecules have various splicing forms in cancer cell systems, utilization in treatment and diagnosis with antibodies corresponding to these forms has been suggested (Patent Literature 9).

However, any of these literatures do not disclose an example regarding an antibody which demonstrates a therapeutic effect on a specific disease by targeting PODXL2. It has not been revealed whether or not an antibody against PODXL2 has an anti-cancer activity.

CITATION LIST

Patent Literatures

[PTL 1] International Publication No. WO2005/054459
[PTL 2] International Publication No. WO2001/034797
[PTL 3] International Publication No. WO2007/102787
[PTL 4] International Publication No. WO2004/109286
[PTL 5] International Publication No. WO2006/113671
[PTL 6] International Publication No. WO2002/079492
[PTL 7] Japanese Unexamined Patent Application Publication No. 2007-14229
[PTL 8] Japanese Patent No. 2932837
[PTL 9] United States Patent Application Publication No. 20060294607

Non Patent Literature

[NPL 1] J. Biol. Chem. 270, 29439-29446 (1995)
[NPL 2] J. Biol. Chem. 272, 15708-15714 (1997)
[NPL 3] Hematopoietic stem cell: from basic to gene therapy, regenerative medicine, Ozawa Keiya editor, Chugai-Igakusha, 2002, pp. 38-45

SUMMARY OF INVENTION

Technical Problem

The present invention has been made in view of such circumstances. An object of the present invention is to provide a novel antibody having an excellent anti-cancer activity. Another object of the present invention is to provide an anti-cancer agent comprising such an antibody as an active ingredient.

Solution to Problem

In order to achieve the above objects, the present inventors, first, prepared a cDNA library derived from GCIY cells of a cancer cell line. By an SST-REX method, a cDNA encoding a protein expressed on a cell surface or secreted from the cell was selected from the cDNA library. Next, monoclonal antibodies against the protein encoded by the selected cDNA were prepared. The in vitro and in vivo anti-cancer activities and binding to various cancer cell lines were examined. As a result, it was found out that an "ACT36-27_5D1" antibody, one of the obtained monoclonal antibodies, bound to a PODXL2 protein and had excellent in vitro and in vivo anti-cancer activities. Further, the present inventors successfully identified a region including an epitope of the antibody, and also determined the amino acid sequences of variable regions of a light chain and a heavy chain. Thus, the present invention was completed.

Specifically, the present invention relates to: a monoclonal antibody which binds to a PODXL2 protein, and which has an anti-cancer activity; and an anti-cancer agent comprising the antibody as an active ingredient. More specifically, the present invention provides:

(1) an antibody which binds to a human-derived PODXL2 protein, and which has an anti-cancer activity;
(2) the antibody according to (1), which binds to an extracellular region of the human-derived PODXL2 protein;
(3) the antibody according to (1), wherein the cancer is gastric cancer;
(4) the antibody according to (1), comprising
  a light chain variable region comprising amino acid sequences of SEQ ID NOs: 3 to 5; and
  a heavy chain variable region comprising amino acid sequences of SEQ ID NOs: 6 to 8;
(5) an antibody comprising the amino acid sequences of SEQ ID NOs: 3 to 8 of the antibody according to (4), in at least one of which one or more amino acids are substituted, deleted, added and/or inserted, and having an equivalent activity to that of the antibody according to (4);
(6) an antibody comprising the amino acid sequences of SEQ ID NOs: 3 to 8 of the antibody according to (4), in at least one of which one or more amino acids are conservatively substituted, and having an equivalent activity to that of the antibody according to (4);
(7) the antibody according to (1), comprising:
  a light chain variable region comprising an amino acid sequence of SEQ ID NO: 10; and
  a heavy chain variable region comprising an amino acid sequence of SEQ ID NO: 12;
(8) an antibody comprising the amino acid sequences of SEQ ID NOs: 10 and 12 of the antibody according to (7), in at least one of which one or more amino acids are substituted, deleted, added and/or inserted, and having an equivalent activity to that of the antibody according to (7);
(9) an antibody comprising the amino acid sequences of SEQ ID NOs: 10 and 12 of the antibody according to (7), in at least one of which one or more amino acids are conservatively substituted, and having an equivalent activity to that of the antibody according to (7);
(10) an antibody comprising the amino acid sequences of SEQ ID NOs: 10 and 12 of the antibody according to (7), from at least one of which a signal sequence is removed, and having an equivalent activity to that of the antibody according to (7);
(11) an antibody which binds to an epitope, of the antibody according to (7), on the human-derived PODXL2 protein, and which has an anti-cancer activity;
(12) a peptide comprising any one of a light chain and a variable region thereof, of the antibody according to (1) comprising amino acid sequences of SEQ ID NOs: 3 to 5;
(13) the peptide according to (12) comprising anyone of:
  an amino acid sequence of SEQ ID NO: 10; and
  an amino acid sequence of SEQ ID NO: 10 from which a signal sequence is removed;

(14) a peptide comprising any one of a heavy chain and a variable region thereof, of the antibody according to (1) comprising amino acid sequences of SEQ ID NOs: 6 to 8;
(15) the peptide according to (14), comprising any one of:
an amino acid sequence of SEQ ID NO: 12; and
an amino acid sequence of SEQ ID NO: 12 from which a signal sequence is removed;
(16) a DNA encoding any one of:
the antibody according to any one of (1) to (10); and
the peptide according to any one of (12) to (15);
(17) a hybridoma which produces the antibody according to any one of (1) to (10), or which comprises the DNA according to (16);
(18) an antibody produced by the hybridoma according to (17);
(19) an anti-cancer agent comprising the antibody according to anyone of (1) to (10) as an active ingredient;
(20) the anti-cancer agent according to (19), wherein the cancer is gastric cancer;
(21) a cancer vaccine composition comprising a human-derived PODXL2 protein or a part thereof; and
(22) the cancer vaccine composition according to (21), wherein the cancer is gastric cancer.

Advantageous Effects of Invention

The present invention provides an antibody which binds to a human-derived PODXL2 protein, and which has excellent in vitro and in vivo anti-cancer activities. The antibody of the present invention can be used for treatment and prevention of cancer. The antibody of the present invention is particularly effective in suppressing growth of gastric cancer cells.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 9 shows a representation illustrating the amino acid sequences of the light chain variable region (SEQ ID NO: 10) and heavy chain variable region (SEQ ID NO: 12) of the ACT36-27_5D1 antibody, and CDR prediction. A broken line indicates the result of the CDR prediction, and a solid line indicates signal sequences of a light chain and a heavy chain.

DESCRIPTION OF EMBODIMENTS

Figure 1:
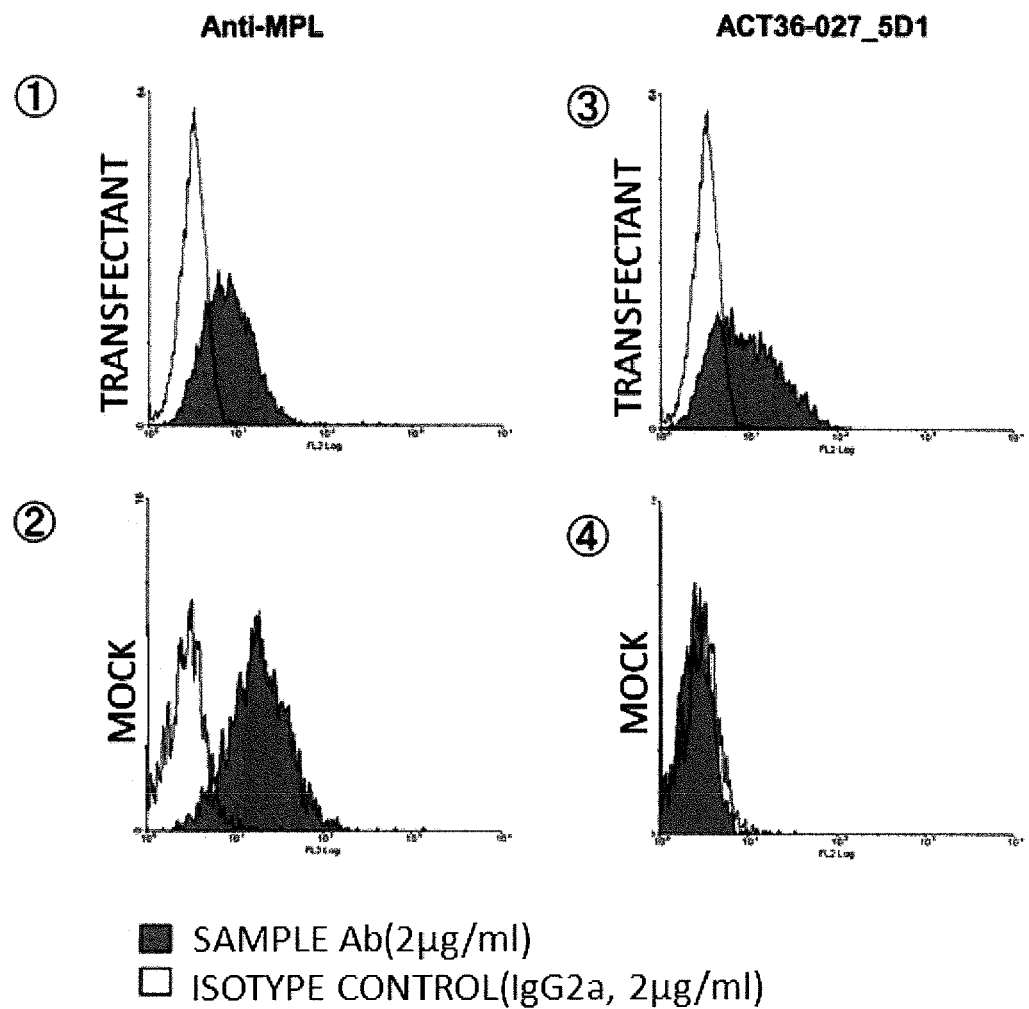
FIG. 1 shows graphs illustrating the reactivity between an ACT36-27_5D1 antibody and a Ba/F3 cell expressing a PODXL2 gene. Reactions of antibodies with the transfectant Ba/F3 cell which is an immunogen cell expressing the full-length PODXL2 gene (transfectant) and another transfectant Ba/F3 cell not expressing the PODXL2 (mock) were analyzed by a flow cytometer. A filled histogram part in each flow cytometer data illustrates the reaction with the corresponding sample antibody, while a white histogram part illustrates a reaction with a mouse IgG2a control.

The present invention provides an antibody which binds to a human-derived PODXL2 protein, and which has an anti-cancer activity. In the present invention, the "antibody" includes all the classes and subclasses of immunoglobulins. The "antibody" includes polyclonal antibodies and monoclonal antibodies, and also means to include the form of a functional fragment of the antibody. The "polyclonal antibody" is an antibody preparation including different antibodies respectively against different epitopes. Meanwhile, the "monoclonal antibody" means an antibody (including an antibody fragment) obtained from a substantially homogeneous population of antibodies. In contrast to the polyclonal antibody, the monoclonal antibody recognizes a single determinant on an antigen. The antibody of the present invention is preferably a monoclonal antibody. The antibody of the present invention is an antibody separated and/or collected (i.e., isolated) from a component in a natural environment.

The "human-derived PODXL2 protein (NM_005397.3; *Homo sapiens* podocalyxin-like (PODXL), transcript variant 2)" to which the antibody of the present invention binds is a type I transmembrane glycoprotein which exists in a cell membrane and which has a highly glycosylated extracellular region. The human-derived PODXL2 protein is a glycoprotein comprising a 526-amino acid sequence, and is assumed to be a single transmembrane protein within which: a part 22-amino acid long from the N terminal is a signal sequence; a part from positions 23 to 429 is an extracellular region; a part from positions 430 to 450 is a transmembrane region; and a part subsequent to position 451 is an integral membrane region. The amino acid sequence of a typical human-derived PODXL2 protein is shown in SEQ ID NO: 2, and the base sequence of the PODXL2 gene is shown in SEQ ID NO: 1. Besides one having such a typical amino acid sequence, the human-derived PODXL2 protein having some amino acid naturally mutated may exist. Thus, the "human-derived PODXL2 protein" in the present invention is preferably a protein comprising the amino acid sequence of SEQ ID NO: 2, and in addition includes one comprising an amino acid sequence represented by SEQ ID NO: 2 in which one or more amino acids are substituted, deleted, inserted, or added. The substitution, deletion, insertion, or addition of the amino acid sequence is generally 10 amino acids or less (for example, 5 amino acids or less, 3 amino acids or less, 1 amino acid).

In the present invention, the "anti-cancer activity" means an activity to suppress in vitro and/or in vivo growth of cancer cells. The anti-cancer activity can be evaluated, for example, by an MTT assay described in Example 7 or analysis using a tumor bearing model described in Example 8. A preferred embodiment of the antibody of the present invention is an antibody which suppresses growth of a gastric cancer cell line (for example, GCIY) by 50% or more (for example, 60% or more, 70% or more) in comparison with a control, 3 hours after the antibody is added in a case of conducting the MTT assay described in Example 7.

Moreover, another preferred embodiment of the antibody of the present invention is an antibody which reduces the tumor volume or the weight of a tumor to be extracted by 50% or more (for example, 60% or more) in comparison with a control, 3 week after the antibody is administered in the analysis using the tumor bearing model described in Example 8. When used as an anticancer agent, these antibodies preferably further have such characteristics as not to reduce the weight of an administration target.

Another preferred embodiment of the antibody of the present invention is an antibody comprising: a light chain variable region comprising light chains CDR1 to CDR3 (amino acid sequences of SEQ ID NOs: 3 to 5); and a heavy chain variable region comprising heavy chains CDR1 to CDR3 (amino acid sequences of SEQ ID NOs: 6 to 8). An example thereof includes an antibody comprising: a light chain variable region comprising an amino acid sequence of SEQ ID NO: 10 (or an amino acid sequence of SEQ ID NO: 10 from which a signal sequence is removed); and a heavy chain variable region comprising an amino acid sequence of SEQ ID NO: 12 (or an amino acid sequence of SEQ ID NO: 12 from which a signal sequence is removed).

Once obtaining the antibody comprising: the light chain variable region comprising the amino acid sequence of SEQ ID NO: 10; and the heavy chain variable region comprising the amino acid sequence of SEQ ID NO: 12, those skilled in the art could produce various antibodies which bind to a peptide region (epitope) specified on the human-derived PODXL2 protein recognized by the antibody and which exhibit an anti-cancer activity. The epitope of the antibody can be determined by well-known methods such as checking binding to an overlapping synthetic oligopeptide obtained from the amino acid sequence of the human-derived PODXL2 protein (for example, Example 10 of the present application, Ed Harlow and D. Lane, Using Antibodies, a Laboratory Manual, Cold Spring Harbor Laboratory Press, U.S. Pat. No. 4,708,871). A peptide library in phage display can be used for the epitope mapping. Whether two antibodies bind to the same epitope or sterically overlapping epitopes can be determined by a competitive assay method. The peptide region on the PODXL2 protein recognized by the antibody of the present invention is preferably an extracellular region of the PODXL2 protein. The peptide region on the PODXL2 protein recognized by the antibody of the present invention is more preferably is a region within a range from positions 400 to 428 of the amino acid sequence of the PODXL2 protein.

The antibody of the present invention includes a chimeric antibody, a humanized antibody, a human antibody, and a functional fragment of these antibodies. In a case where the antibody of the present invention is administered as a drug to a human, a chimeric antibody, a humanized antibody, or a human antibody is desirable from the viewpoint of reducing side effect.

In the present invention, the "chimeric antibody" is an antibody obtained by linking a variable region of an antibody of one species with a constant region of an antibody of another species. A chimeric antibody can be obtained as follows, for example. A mouse is immunized with an antigen. A portion corresponding to an antibody variable part (variable region) which binds to the antigen is cut out from a gene of a monoclonal antibody of the mouse, and ligated to a gene of an antibody constant part (constant region) derived from human bone marrow. These genes are incorporated into an expression vector and introduced into a host which produces the chimeric antibody (for example, Japanese Unexamined Patent Application Publication No. Hei 8-280387, U.S. Pat. No. 4,816,397, U.S. Pat. No. 4,816,567, U.S. Pat. No. 5,807, 715). Meanwhile, in the present invention, the "humanized antibody" is an antibody obtained by grafting a gene sequence of an antigen binding site (CDR) of a non-human-derived antibody onto a gene of a human antibody (CDR grafting). A preparation method thereof is known (see, for example, EP239400, EP125023, WO90/07861, WO96/02576). In the present invention, the "human antibody" is an antibody of which all the regions are derived from human. For preparation of a human antibody, a transgenic animal (for example, a mouse) capable of producing a repertoire of human antibodies by immunization can be utilized. A preparation method of a human antibody is known (for example, Nature, 1993, 362, 255-258, Intern. Rev. Immunol, 1995, 13, 65-93, J. Mol. Biol, 1991, 222, 581-597, Nature Genetics, 1997, 15, 146-156, Proc. Natl. Acad. Sci. USA, 2000, 97: 722-727, Japanese Unexamined Patent Application Publication No. Hei 10-146194, Japanese Unexamined Patent Application Publication No. Hei 10-155492, Japanese Patent No. 2938569, Japanese Unexamined Patent Application Publication No. Hei 11-206387, International Application Japanese-Phase Publication No. Hei 8-509612, International Application Japanese-Phase Publication No. Hei 11-505107).

In the present invention, the "functional fragment" of the antibodies means a part of an antibody (a partial fragment), which specifically recognizes the human-derived PODXL2 protein. Specific examples thereof include Fab, Fab', F(ab')$_2$, a variable region fragment (Fv), disulfide-bonded Fv, single chain Fv (scFv), sc(Fv)$_2$, a diabody, a polyspecific antibody, polymers thereof, and the like.

Here, the "Fab" means a monovalent antigen-binding fragment of an immunoglobulin, which is formed of a part of one light chain and a part of one heavy chain. The Fab can be obtained by papain digestion of an antibody, or by a recombinant method. The "Fab'" differs from the Fab in that a small number of residues including one or more cysteines from a hinge region of an antibody are added to the carboxy terminus of a heavy chain CH1 domain. The "F(ab')2" means a divalent antigen-binding fragment of an immunoglobulin, which is formed of parts of both light chains and parts of both heavy chains.

The "variable region fragment (Fv)" is a smallest antibody fragment having a complete antigen recognition and binding site. The Fv is a dimer in which a heavy chain variable region and a light chain variable region are strongly linked by non-covalent bonding. An antibody derived from animals belonging to Camelidae (for example, *Camelus dromedarius, Camelus bactrianus*, Lama, *Vicugna pacos, Vicugna vicugna*) is capable of recognizing an antigen only by means of a heavy chain variable region (VHH), and is called a "nanoantibody." The antibody of the present invention may be a nanoantibody.

The "single chain Fv (sFv)" includes a heavy chain variable region and a light chain variable region of an antibody, and these regions exist in a single polypeptide chain. The "sc(Fv)2" is a single chain obtained by bonding two heavy chain variable regions and two light chain variable regions with a linker or the like. The "diabody" is a small antibody fragment having two antigen binding sites. The fragment includes a heavy chain variable region bonded to a light chain variable region in a single polypeptide chain, and each of the regions forms a pair with a complementary region of another chain. The "polyspecific antibody" is a monoclonal antibody having binding specificity to at least two different antigens. For example, a polyspecific antibody can be prepared by co-expression of two immunoglobulin heavy chain/light chain pairs in which two heavy chains have mutually different specificities.

The present invention provides a peptide comprising any one of a light chain, a heavy chain, and variable regions thereof, of an antibody including a CDR identified in the present invention. A preferable peptide is a peptide comprising any one of a light chain and a variable region thereof, of the antibody of the present invention comprising the amino acid sequences of SEQ ID NOs: 3 to 5, and particularly preferably a peptide comprising any one of the amino acid sequence of SEQ ID NO: 10 and an amino acid sequence of SEQ ID NO: 10 from which a signal sequence is removed. Another preferable peptide is a peptide comprising a heavy chain and a variable region thereof, of the antibody of the present invention comprising amino acid sequences of SEQ ID NOs: 6 to 8, and particularly preferably a peptide comprising any one of the amino acid sequence of SEQ ID NO: 12 and an amino acid sequence of SEQ ID NO: 12 from which a signal sequence is removed. A functional antibody can be prepared, for example, by linking these peptides with a linker or the like.

The antibody of the present invention includes an antibody whose amino acid sequence is modified without impairing desirable activities (binding activity to an antigen, anti-cancer activity, and/or other biological characteristics). An amino acid sequence variant of the antibody of the present invention can be prepared by introducing mutation in a DNA encoding an antibody chain of the present invention or by peptide synthesis. Such modification includes, for example, substitution, deletion, addition and/or insertion of a residue in an amino acid sequence of the antibody of the present invention. A modified site of the amino acid sequence of the antibody may be a constant region of a heavy chain or a light chain of the antibody or a variable region (framework region and CDR) thereof, as long as the resulting antibody has an equivalent activity to that of the antibody before the modification. Presumably, modification of amino acids other than the CDR has a relatively small influence on binding affinity for an antigen. Meanwhile, there are currently known methods of screening for antibodies whose affinity for an antigen is enhanced by modification of amino acids in the CDR (PNAS, 102, 8466-8471 (2005), Protein Engineering, Design & Selection, 21, 485-493 (2008), International Publication No. WO2002/051870, J. Biol. Chem., 280, 24880-24887 (2005), Protein Engineering, Design & Selection, 21, 345-351 (2008)).

The number of amino acids modified is preferably 10 amino acids or less, more preferably 5 amino acids or less, and most preferably 3 amino acids or less (for example, 2 amino acid or less, or 1 amino acid). The modification of amino acids is preferably conservative substitution. In the present invention, the "conservative substitution" means substitution with another amino acid residue having a chemically similar side chain. Groups of amino acid residues having chemically similar amino acid side chains are well known in the technical field to which the present invention pertains. For example, amino acid residues can be grouped into acidic amino acids (aspartic acid and glutamic acid), basic amino acids (lysine, arginine, histidine), and neutral amino acids. The neutral amino acids can be classified into amino acids having a hydrocarbon chain (glycine, alanine, valine, leucine, isoleucine, proline), amino acids having a hydroxy group (serine, threonine), amino acids containing sulfur (cysteine, methionine), amino acids having an amide group (asparagine, glutamine), an amino acid having an imino group (proline), and amino acids having an aromatic group (phenylalanine, tyrosine, tryptophan). In addition, the phrase "having an equivalent activity" means the binding activity to an antigen or the anti-cancer activity is equivalent (for example, 70% or more, preferably 80% or more, more preferably 900 or more) to that of a target antibody (typically, ACT36-27_5D1 antibody). The binding activity to an antigen can be evaluated, for example, by preparing a Ba/F3 cell expressing an antigen and analyzing the reactivity with an antibody sample using a flow cytometer (Examples 4, 10). Meanwhile, the anti-cancer activity can be evaluated, for example, by the MTT assay described in Example 7 or analysis using the tumor bearing model described in Example 8, as described above.

Moreover, the modification on the antibody of the present invention may be modification in post-translational process of the antibody such as, for example, alternation of the number or position of the glycosylation sites. Thereby, for example, the ADCC activity of the antibody can be improved. Glycosylation of the antibody is typically N-linked or O-linked glycosylation. The glycosylation of the antibody largely depends on a host cell used for expression of the antibody. Modification of the glycosylation pattern can be made by known methods such as introduction or deletion of a certain enzyme which involves in carbohydrate production (Japanese Unexamined Patent Application Publication No. 2008-113663, U.S. Pat. No. 5,047,335, U.S. Pat. No. 5,510, 261, U.S. Pat. No. 5,278,299, International Publication No. WO99/54342). Further, in the present invention, for the purpose of increasing the stability of the antibody or other purposes, deamidation may be prevented by substituting an amino acid subjected to deamidation or an amino acid adjacent to the amino acid subjected to the deamidation with a different amino acid. Moreover, a glutamic acid can be substituted with a different amino acid to thereby increase the stability of the antibody. The present invention also provides an antibody thus stabilized.

When the antibody of the present invention is a polyclonal antibody, the polyclonal antibody can be obtained as follows. Specifically, an immune animal is immunized with an antigen (human-derived PODXL2 protein, a partial peptide thereof, cells expressing these, or the like). An antiserum from the animal is purified by conventional means (for example, salting-out, centrifugation, dialysis, column chromatography, or the like) to obtain a polyclonal antibody. Meanwhile, the monoclonal antibody can be prepared by a hybridoma method or a recombinant DNA method.

A typical example of the hybridoma method is a Kohler and Milstein method (Kohler & Milstein, Nature, 1975, vol. 256, p. 495). Antibody-producing cells used in the cell fusion process of this method are spleen cells, lymph node cells, peripheral blood leukocytes, and the like of an animal (for example, mouse, rat, hamster, rabbit, monkey, goat) which is immunized with an antigen (human-derived PODXL2 protein, a partial peptide thereof, cells expressing these, or the like). It is also possible to use antibody-producing cells obtained by causing an antigen to act, in a medium, on the cells described above, lymphocytes, or the like which are isolated in advance from a non-immunized animal. As myeloma cells, various known cell lines can be used. If fusible, the antibody-producing cells and the myeloma cells may be originated from different animal species. However, the antibody-producing cells and the myeloma cells are preferably originated from the same animal species. Hybridomas can be produced, for example, by cell fusion between mouse myeloma cells and spleen cells obtained from a mouse immunized with an antigen. Thereafter, by screening the hybridomas, a hybridoma which produces a monoclonal antibody specific to the human-derived PODXL2 protein can be obtained. The monoclonal antibody against the human-derived PODXL2 protein can be obtained by culturing the hybridoma, or from an ascites in a mammal to which the hybridoma is administered.

The recombinant DNA method by which the above-described antibody of the present invention is produced as a recombinant antibody is a method as follows. Specifically, a DNA encoding the antibody or the peptide of the present invention is cloned from a hybridoma, B cell, or the like. The cloned DNA is incorporated into an appropriate vector, and is introduced into a host cell (for example, a mammalian cell line, *Escherichia coli*, yeast cell, insect cell, plant cell, or the like) (for example, P. J. Delves, Antibody Production: Essential Techniques, 1997 WILEY, P. Shepherd and C. Dean Monoclonal Antibodies, 2000 OXFORD UNIVERSITY PRESS, Vandamme A. M. et al., Eur. J. Biochem. 192: 767-775 (1990)). For expression of the DNA encoding the antibody of the present invention, DNAs respectively encoding a heavy chain and a light chain may be incorporated into different expression vectors to transform the host cell. Alternatively, the DNAs respectively encoding a heavy chain and a light chain may be incorporated into a single expression vector to transform the host cell (see WO94/11523). The antibody of the present invention can be obtained in a substantially pure and homogeneous form by separation and purification in the host cell cultured in advance or from the culture liquid. For the separation and purification of the antibody, methods normally used for purification of a polypeptide can be used. When a transgenic animal (cattle, goat, sheep, pig, or the like) having an antibody gene incorporated is prepared using a transgenic animal preparation technique, a large amount of a monoclonal antibody derived from the antibody gene can also be obtained from milk of the transgenic animal.

The present invention also provides a DNA encoding the above-described antibody or peptide of the present invention, a vector comprising the DNA, a host cell comprising the DNA, and a method of producing an antibody, the method comprising culturing the host cell and collecting an antibody.

Since having an anti-cancer activity, the antibody of the present invention can be used for treatment or prevention of cancer. Thus, the present invention also provides a method for treating or preventing cancer, the method comprising a step of administering a therapeutically or preventively effective amount of the antibody of the present invention and an anti-cancer agent comprising the antibody of the present invention as an active ingredient to a mammal including human. The treatment or prevention method of the present invention is applicable to various mammals, other than human, including, for example, dogs, cats, cattle, horses, sheep, pigs, goats, rabbits, and the like.

In the present Examples, the antibody of the present invention strongly suppressed growth of, particularly, gastric cancer cells among cancers, and thus particularly effective in treating or preventing gastric cancer (for example, scirrhous gastric cancer).

The anti-cancer agent comprising the antibody of the present invention as an active ingredient can be used in the form of a composition comprising the antibody of the present invention and another component, for example, a saline, an aqueous glucose solution, a phosphate buffer, or the like. The anti-cancer agent of the present invention may be formulated in a liquid or lyophilized form as necessary, and may optionally comprise a pharmaceutically acceptable carrier or medium, for example, a stabilizer, a preservative, an isotonic agent, or the like.

Examples of the pharmaceutically acceptable carrier can include: mannitol, lactose, saccharose, human albumin, and the like for a lyophilized preparation; and a saline, water for injection, phosphate buffer, aluminium hydroxide, and the like for a liquid preparation. However, the examples are not limited to these.

The method of administering the anti-cancer agent may differ depending on the age, weight, sex, general health state of an administration target, and the like. The administration may be carried out by any administration route: oral administration and parenteral administration (for example, intravenous administration, intraarterial administration, local administration). A preferable administration method is parenteral administration. The dose of the anti-cancer agent to be administered varies depending on the age, weight, sex, and general health state of a patient, the severity of cancer progression, and components of the anti-cancer agent to be administered. The dose is generally 0.1 to 1000 mg, and preferably 1 to 100 mg, per kg body weight for an adult per day for intravenous administration.

Since having an activity to bind to a cell surface of a cancer cell, the antibody of the present invention is presumably applicable not only to treatment and prevention of cancer but also to diagnosis of cancer. When the antibody of the present invention is used for diagnosis of cancer or used for detection of a tumor site in cancer treatment, the antibody of the present invention may be labeled. As the label, for example, radioactive substances, fluorescence dyes, chemoluminescent substances, enzymes, coenzymes can be used. Specifically, examples thereof include radioisotopes, fluorescein, rhodamine, dansyl chloride, luciferase, peroxidase, alkaline phosphatase, lysozyme, biotin/avidin, and the like. When the antibody of the present invention is prepared as a diagnostic agent, the diagnostic agent can be obtained in any dosage form by adopting any means suitable for its purpose. For example, after a purified antibody is measured for the antibody titer and is appropriately diluted with PBS (phosphate buffer containing a saline) or the like, a preservative such as 0.1% sodium azide can be added thereto. Alternatively, for example, the antibody of the present invention adsorbed to latex or the like may be used after determined for the antibody titer and appropriately diluted, followed by addition of the preservative.

Furthermore, it has been revealed in the present invention that the antibody against the PODXL2 protein has an anti-cancer activity. Accordingly, the PODXL2 protein or a partial peptide thereof can be administered as a cancer vaccine to a mammal including human (see, for example, Japanese Unexamined Patent Application Publication No. 2007-277251 and Japanese Unexamined Patent Application Publication No. 2006-052216). The present invention also provides a cancer vaccine composition for use as such a cancer vaccine, the cancer vaccine composition comprising a PODXL2 protein or a partial peptide thereof. When formulated, the cancer vaccine composition may comprise a pharmaceutically acceptable carrier or medium, for example, a stabilizer, a preservative, an isotonic agent, or the like, as in the above-described anti-cancer agent of the present invention.

EXAMPLES

Hereinafter, the present invention will be described in more details by way of Examples, but the present invention is not limited to these Examples.

Example 1

Executing SST-REX

SST-REX was executed to comprehensively obtain information on a secretion gene or a membrane expressed on the cell surface of GCIY cells of an established cell line of scirrhous gastric cancer.

(1) Preparation of cDNA

In 1 ml of Trizol (Invitrogen, #15596-026), $2\times10^7$ GCIY cells were suspended and left for 5 minutes, and 200 µl of chloroform was added thereto, followed by suspension for 15 seconds and centrifugation at 12,000×g for 15 minutes. This supernatant after the centrifugation and 500 µl of isopropanol were mixed together, followed by centrifugation at 12,000×g for 10 minutes. The resulting pellets were washed with 80% ethanol, and 200 µg or more of total RNAs were obtained for use in the following experiments.

All of the obtained total RNAs were dissolved in 100 µl of water. Using FastTrack 2.0 mRNA Isolation kit (Invitrogen, #K1593-02), 3 µg of mRNA was obtained. Using SuperScript™ Choice System (invitorgen, #18090-019), double-stranded cDNAs were prepared from the obtained mRNA.

Note that the GCIY cells are from a gastric cancer cell line established from a translucent yellow ascites with yellow blood obtained during the surgery performed on a woman having Borrmann type IV gastric cancer and the peritoneal metastasis. The GCIY cell is a poorly differentiated adenocarcinoma cell from which expression of a multidrug resistance gene (mdr-1) and secretions of CEA, CA19-9, and αFP are observed.

(2) Incorporation of cDNA Sequence into pMX-SST Vector (Chimerization)

To incorporate the obtained cDNA into a retrovirus vector pMX-SST, 5 µg of a pMX-SST vector (Nature Biotechnology 17, p 487-490, 1999) was treated using a restriction enzyme BstXI in 100 µl of a reaction system at 45° for 4 hours. When all the reaction solution was electrophoresed on a 1% agarose gel, DNA fragments of approximately 5000 bases in length and DNA fragments of approximately 500 bases in length were detected. A portion containing the DNA fragments of approximately 5000 bases in length were cut out from the agarose gel. Further, using Wizard® SV Gel and PCR Clean-Up System (promega, #A9282), the DNA fragments of approximately 5000 bases in length were purified. The DNA fragments thus obtained were of the pMX-SST vector treated with the BstXI restriction enzyme, and an aqueous solution containing 50 ng of the DNA fragments per µl was prepared.

The double-stranded cDNAs prepared in advance has blunt ends, and cannot be ligated to the pMX-SST treated with the BstXI restriction enzyme. Thus, an operation was performed, so that the double-stranded cDNAs had the same DNA sequence as one treated with the BstXI restriction enzyme. The double-stranded cDNAs were dissolved in a BstXI Adapter aqueous solution which had been obtained by dissolving 9 µg of BstXI Adapter (invitorgen, #N408-18) in 10 µl of water. To this, 5 µl of Ligation High (TOYOBO, #LGK-201) was added, followed by suspension for reaction at 16° for 16 hours. Thereby, the BstXI Adapter and the double-stranded cDNAs were ligated. Thereafter, using size fractionation columns accompanying SuperScript™ Choice System (invitorgen, #18090-019), DNA fragments having a chain length of approximately 400 bases or less were removed. After that, 3 M sodium acetate in an amount of one tenth of the resulting capacity and ethanol 2.5 times the amount of the capacity were added, and mixed by inverting, followed by centrifugation at 20,400×g for 30 minutes. A precipitate obtained by removing a supernatant after the centrifugation was dissolved in 15 µl of water, and electrophoresed on a 1.5% agarose gel. Then, a gel containing the ligated product of the BstXI Adapter and the double-stranded cDNA fragments having a length of approximately 500 bases to approximately 4000 bases was taken out. Further, using Wizard® SV Gel and PCR Clean-Up System (promega, #A9282), the ligated product of the double-stranded cDNAs and the BstXI Adapter was purified.

In 20 µl of a reaction system, 50 ng of the pMX-SST vector treated with the BstXI restriction enzyme, the total amount of the obtained ligated product of the double-stranded cDNAs and the BstXI Adapter, and T4 DNA ligase were treated at room temperature for 3 hours. The pMX-SST vector treated with the BstXI restriction enzyme was ligated to the ligated product. The composition of the reaction solution was adjusted according to the specification.

(3) Amplification of cDNA Libraries

The cDNA libraries thus constructed using the pMX-SST vector were introduced and amplified in *Escherichia coli*. To the cDNA libraries, 5 µg of tRNA, 12.5 µl of 7.5 M sodium acetate, and 70 µl of ethanol were added, mixed by inverting, followed by centrifugation at 20,400×g for 30 minutes. A supernatant was discarded, and a precipitate was obtained. To the obtained precipitate, 500 µl of 70% ethanol was added, followed by centrifugation at 20,400×g for 5 minutes. A precipitate obtained by discarding a supernatant was dissolved in 10 µl of water. To amplify the cDNAs in *Escherichia coli*, 2 µl of the solution was mixed with 23 µl of competent cell (Invitrogen, #18920-015), followed by electroporation under a condition of 1.8 kV. A total amount of the resulting solution was suspended in 1 ml of an SOC medium (Invitrogen, #15544-034). This operation was performed twice. The SOC medium in which *Escherichia coli* was suspended was subjected to shaking culture at 37° for 90 minutes. Thereafter, a total amount of this culture solution was inputted into 500 ml of a LB medium containing 100 µg of ampicillin per ml of the medium, and was subjected to shaking culture at 37° for 16 hours.

To check the number of cDNA libraries introduced to *Escherichia coli* and the chain length of the cDNAs ligated to the pMX-SST vector, 5 µl of the culture liquid was taken out and plated on a LB agar medium containing 50 µg/ml of ampicillin.

As a result, growth of 150 colonies was observed on the 5 µl-plated LB agar medium. This suggested that there were $1.5 \times 10^7$ independent cDNA libraries in 500 ml of the culture liquid. Moreover, plasmids were extracted from certain 16 of the colonies, and subjected to a restriction enzyme treatment with a restriction enzyme BstXI. The treated product was electrophoresed on a 1% agarose gel, and the length of the cDNAs on the pMX-SST vector was measured. As a result, an average value thereof was approximately 1000 bases.

Plasmids collected from the remaining culture liquid were purified using 10 NucleoBond® AX 500 columns (NIPPON Genetics Co., Ltd., #740574), and the amplified cDNA library system was established.

(4) Packaging of cDNA libraries and Executing SST-REX Method

To produce a retrovirus containing a pMX-SST retrovirus vector RNA into which a gene derived from the cDNA library was incorporated, $2 \times 10^6$ virus packaging cells Plat-E (Gene Ther. 2000 June; 7 (12): 1063-6.) were suspended in a 6-cm dish containing 4 ml of DMEM medium (Wako, #044-29765), and cultured under conditions of 37° and 5% $CO_2$ for 24 hours. Meanwhile, 100 µl of opti-MEM (GIBCO, #31985070) and 9 µl of Fugene (Roche, #1814443) were mixed and left for 5 minutes at room temperature. Then, 3 µg of the cDNA libraries were added thereto and left for 15 minutes at room temperature. The solution containing the cDNA libraries was dropped to the cultured Plat-E cells. After 24 hours, a supernatant was replaced, and the culturing was continued under the same conditions. A supernatant after another 24 hours was filtered through a 0.45-µm filter.

Into a 10-cm dish having a 9.5 ml of a RPMI-1640 medium (Kohjin Bio Co., Ltd.) containing $4 \times 10^6$ Ba/F3 cells, 0.5 ml of the filtered supernatant thus obtained was added.

Further, 10 µl of polybrene (CHEMICON, #TR-1003-G) and 10 ng of IL-3 were added, followed by culturing for 24 hours. Then, the cells were washed with a RPMI-1640 medium three times, and suspended in 200 ml of a fresh RPMI-1640 medium. The cells were spread in an equal amount on each of twenty 96-well plates. Selection and cloning were attempted based on the autonomous replication ability of the Ba/F3 cells. Cells whose growth was observed after 10 days to 20 days were selected based on the SST-REX, and culturing was further continued until each well became full of the grown cells.

(5) Analysis of Gene Product Obtained by SST-REX

Half the amount of the cells obtained from each well was cultured to expand as cell stocks. Further, the cells from the cell stocks were cultured. A transfectant Ba/F3 cell extracellularly expressing a peptide molecule derived from the incorporated cDNAs was used as an immunogen cell for preparing an antibody and as a screening target cell. A genome was extracted from the other half of the cells obtained from each well, followed by sequencing to analyze the gene derived from the introduced cDNAs. In the sequencing, PCR was performed on the obtained genome using LA taq DNA polymerase (Takara, #RR002) or PrimeSTAR MAX DNA polymerase (TaKaRa, #R045A). PCR primers used had the following sequences.

```
SST3'-T7
                                         (SEQ ID NO: 13)
5'-TAATACGACTCACTATAGGGCGCGCAGCTGTAAACGGTAG-3'

SST5'-T3
                                         (SEQ ID NO: 14)
5'-ATTAACCCTCACTAAAGGGAGGGGGTGGACCATCCTCTA-3'
```

The PCR products were purified using Wizard® SV Gel and PCR Clean-Up System (promega, #A9282) and so forth. Then, the purified PCR products were sequenced using Big-Dye Terminator v3.1 Cycle sequencing (ABI, #4337456) and DNA sequencer ABI3100XL. The following was used as a primer in the sequencing.

```
SST5'-T3
                                         (SEQ ID NO: 15)
5'-ATTAACCCTCACTAAAGGGAGGGGGTGGACCATCCTCTA-3'
```

The obtained sequence data was analyzed using a BLAST search (ncbi.nlm.nih.gov/BLAST/) and SignalP 3.0 Server (cbs.dtu.dk/services/SignalP/).

As a result of executing the SST-REX method using the cells as the material as described above, cDNA-derived genes from 87 transfectant Ba/F3 cells were sequenced in the first execution, and 40 different genes were obtained. In the second execution, cDNA-derived genes from 176 transfectant Ba/F3 cells were sequenced, and 56 different genes were obtained. Note that 15 genes were overlapped between the first and second executions. Thus, 81 cDNA-derived genes were obtained in total by the two executions. The transfectant Ba/F3 cell system subjected to the gene analysis was confirmed to contain only one gene derived from the cDNA, and used for the subsequent experiments (hereinafter, the cell containing the cDNA-derived gene thus obtained is referred to as a "SST clone cell").

Example 2

Cloning of PODXL2 Full-Length Gene and Establishment of Ba/F3 Cell Line Expressing the Same Further, a PODXL2 gene included in the cDNA-derived gene list obtained in Example 1 was cloned to obtain SST clone cells containing the full-length gene.

A PCR reaction was performed using a design primer based on the information on NM_005397 in the nucleotide search site (ncbi.nlm.nih.gov/nucleotide) of NCBI and PrimeSTAR MAX DNA polymerase (TaKaRa, #R045A) with 30 ng of the cDNAs from the GCIY cells prepared by SST-REX as a template.

```
Forward primer:
                                        (SEQ ID NO: 16)
ccggaattcagaggcgacgacacgatgcg Reverse primer:
                                        (SEQ ID NO: 17)
ttttccttttgcggccgcgaggtgtgtgtcttcctcct
```

The PCR products thus obtained were electrophoresed on a 1% agarose gel, and DNA fragments of a target length were extracted from the gel. The extracted DNA fragments were treated with EcoRI (TaKaRa, #1040A) and NotI (TaKaRa, #1166A) restriction enzymes. Concurrently, a pMX-SST vector was also treated with EcoRI and NotI restriction enzymes. Using Ligation High (TOYOBO, #LGK-201), 100 ng of the DNA fragments and 40 ng of the pMX-SST vector which were treated with the restriction enzymes were ligated for 2 hours.

To a total amount of those ligated, 100 µl of heat shock $Escherichia\ coli$ competent cells were added and left on ice for 30 minutes, followed by incubation at 42° for 90 seconds. Then, 1 ml of a LB medium was added thereto, followed by incubation at 37° for 1 hour. Subsequently, a supernatant was removed by centrifugation at 15,000×g for 1 minute. $Escherichia\ coli$ pellets were suspended in the resultant liquid. A total amount of this was spread over a LB agar medium containing ampicillin by 50 µg/mL, and incubated at 37° overnight. Using the resultant colonies, PCR and sequence analysis were performed by the same methods as the sequence analysis in Example 1 (4). The PCR product of a clone which was confirmed to have the DNA fragment of a target length was sequenced, and it was confirmed that the target sequence was inserted. Note that as the PCR polymerase in the sequence analysis, PrimeSTAR MAX DNA polymerase was used.

Then, the colonies in which the target sequence was inserted were inoculated in 3 ml of a LB liquid medium and cultured at 37° overnight. A total amount of the culture was centrifuged at 3,000×g for 15 minutes. A supernatant was removed, and purified using QuickLyse Miniprep Kit (QIAGEN, #27406). Thus, plasmids containing the full-length PODXL2 gene were obtained.

Subsequently, a retrovirus containing a vector was prepared using the obtained plasmids by the same operations as those after the packaging of the cDNA libraries illustrated in Example 1 (4) and thereafter. After that, a Ba/F3 cell line expressing the full-length PODXL2 gene was established for use in the subsequent experiments.

Example 3

Preparation of PODXL2 Monoclonal Antibody

As an immune animal, a mouse Balb/c was used. First, as an immunostimulant, TiterMax Gold (Alexis Biochemicals, ALX-510-002-L010) was mixed with PBS in an equivalent amount thereto and emulsified. To the immune animal, 50 µl of the emulsified product was administered. On the next day, $5 \times 10^6$ SST clone cells having the PODXL2 gene were administered thereto as immunogen cells. Further, the immunogen cells were injected every 2 days 4 times. Approximately 2 weeks after the first immunization, secondary lymphoid tissues were extracted and ground to obtain a cell population including antibody-producing cells. These cells were mixed with fusion partner cells for cell fusion using polyethylene glycol (MERCK, 1.09727.0100). Thereby, hybridomas were prepared. As the fusion partner cells, mouse myeloma cells P3U1 (P3-X63-Ag8.U1) were used.

The hybridomas were cultured in a RPMI 1640 selective medium (Wako) containing HAT (SIGMA, H0262), 5% BM-condimed (Roche, 663573), 15% FBS, and 1% penicillin/streptomycin solution (GIBCO, 15140-122) for 10 to 14 days. Then, by the flow cytometry described in Example 4, hybridomas which reacted with the immunogen cell, but which did not react with an SST clone cell not containing the antigen gene as the immunogen cell (negative control cell), were selected. The hybridomas were subjected to limiting dilution, and thereby monoclonal hybridoma clones producing an anti-PODXL2 antibody ACT36-27_5D1 were obtained (FIG. 1).

The obtained hybridomas were maintained using an RPMI-1640 medium containing required amounts of HT (SIGMA, HT media supplement (50×) Hybri-Max (Sigma-Aldrich, H0137)), 15% FBS, and 1% penicillin/streptomycin solution (GIBCO, 15140-122). An isotype of the antibody to be produced was determined using Iso Strip Kit (Roche, 1493027). As a result, the isotype was IgG2a/K.

The ACT36-27_5D1 antibody purified from the resultant monoclonal hybridomas was obtained as follows. The hybridomas were acclimatized to a serum-free medium (Hybridoma-SFM: GIBCO, 12045-076) and cultured to expand. After culturing for a certain period, a culture supernatant was obtained. Next, IgG fractions contained in the culture supernatant were purified using Protein A Sepharose (GE healthcare Life Sciences, 17-1279-03), MAPS-II Binding Buffer (BIO-RAD, 153-6161), and MAPS-II Elution Buffer (BIO-RAD, 153-6162). The eluted IgGs were dialyzed with PBS, and purified antibody fractions were obtained.

Example 4

Antibody Screening Using Flow Cytometry

The reactivity between the ACT36-27_5D1 antibody and various cells (a Ba/F3 cell expressing the target gene, a Ba/F3 cell not expressing the target gene, various cancer cells, and so forth) was analyzed using flow cytometry.

In this Example, as a cell suspension buffer and subsequent wash buffer, 2 mM EDTA and PBS containing 0.5% BSA were used. The various cells (target cells) to react with the antibody were adjusted and dispensed into a 96-hole plate (BD Falcon, 353911) in such a manner that 100 µl of the cell suspension containing $5 \times 10^4$ cells was in one well.

Moreover, in a case where cells to be stained were from a cancer cell line, when at 80% confluency, the cells were detached from the culture plate using Cell Dissociation Buffer (GIBCO, 13151-014) and collected.

To each sample of the cell suspension, 50 µl of the hybridoma culture supernatant or 2-µg/ml of the purified antibody (hereinafter, referred to as an "antibody solution") was added, and the antibody was reacted with the cells. As an isotype control of the antibody solution, a wash buffer containing 2 µg/ml of each of mouse IgG1 (BioLegend, 400412), mouse IgG2a (BioLegend, 400224), and mouse IgG2b (BioLegend, 400324) was used. The hybridoma culture supernatant was reacted with the target cells at room temperature for 30 minutes, followed by centrifugation at 700×g for 2 minutes. Then, a culture supernatant was removed. Further, 100 µl of a wash buffer was added, followed by centrifugation at 700×g for 2 minutes again. A supernatant was removed. Then, the cells were washed.

Next, to the cell pellets after the washing, 50 µl of Goat anti-mouse IgG, F(ab') 2-PE (PE=phycoerythrin, Beckman Coulter, IM0855) diluted 200-fold with a wash buffer was added as a secondary antibody for detection, and reacted in the dark at room temperature for 30 minutes. The reaction was followed by centrifugation at 700×g for 2 minutes. A supernatant was removed. Further, 100 µl of a wash buffer was added, followed by centrifugation at 700×g for 2 minutes again. A supernatant was removed. Then, the cells were washed. Thereafter, the cells were suspended in an appropriate amount of a wash buffer. The reactivity between the antibody and the cells was analyzed by a flow cytometer (Beckman Coulter, FC500 MPL).

In measuring the reactivity, gates were set in such a manner that living cells were selected according to measurement values of forward scatter and side scatter. The fluorescence intensity of PE was measured based on the reactivity of the selected living cells with the antibody. With reference to the reaction strengths of the isotype controls, a hybridoma cell which produced a culture supernatant demonstrating significant reactivity with the immunogen cell but not demonstrating the reactivity with the negative control cells was selected as a candidate clone.

In the reactivity analysis between the antibody and the various cells, with reference to the reaction strength with the antibody and with isotype control antibodies, an antibody demonstrating significant reactivity was selected.

Example 5

Flow Cytometry Using Cancer Cells

Figure 2:
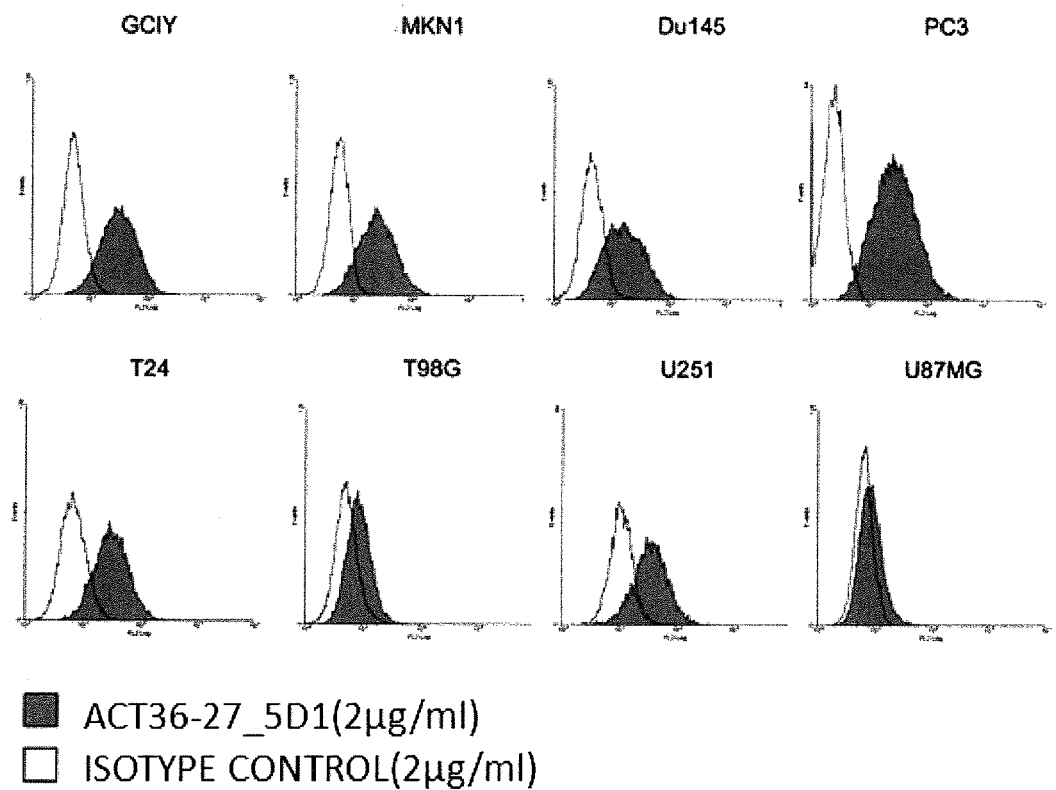
FIG. 2 shows graphs illustrating the result of analyzing, by flow cytometer, the reactivity between the ACT36-27_5D1 antibody and various cultured cancer cells. A filled histogram part in each flow cytometer data illustrates the reaction with the corresponding sample antibody, while a white histogram part illustrates the reaction with mouse IgG2a used as the control. As the target cancer cell lines, gastric cancer cell lines (GCIY, MKN1), a bladder cancer cell line (T24), prostate cancer cell lines (Du145, PC3), and glioma cell lines (T98G, U251, U87MG) were used.
Figure 3A:
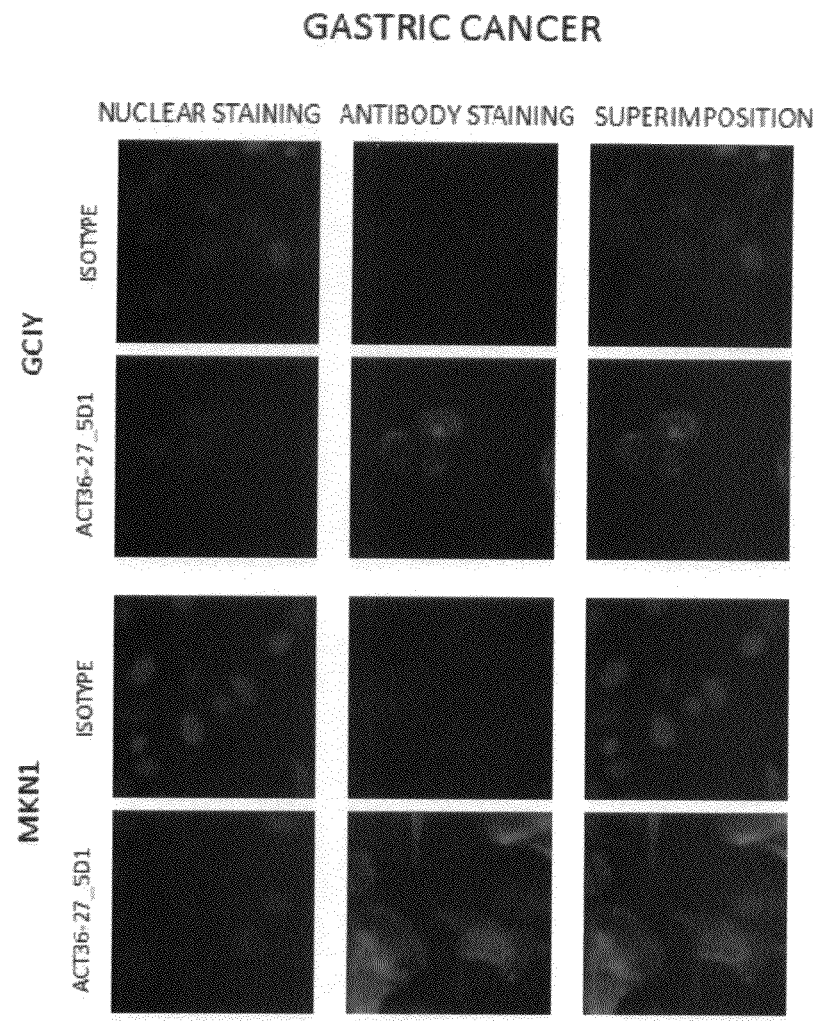
FIG. 3A shows graphs illustrating the result of analyzing, by cell staining, the reactivity between the ACT36-27_5D1 antibody and the surfaces of the various cultured cancer cells. As the cancer cell lines, the gastric cancer cell lines (GCIY, MKN1) were used. The graphs on the left show nuclear staining images by using Hoechst 33342. The graphs in the center show staining images by the antibody. The graphs on the right show superimposed images of the nuclear staining images by using Hoechst 33342 on the staining images by the antibody (the same shall apply hereinafter to FIGS. 3B to F).
Figure 3B:
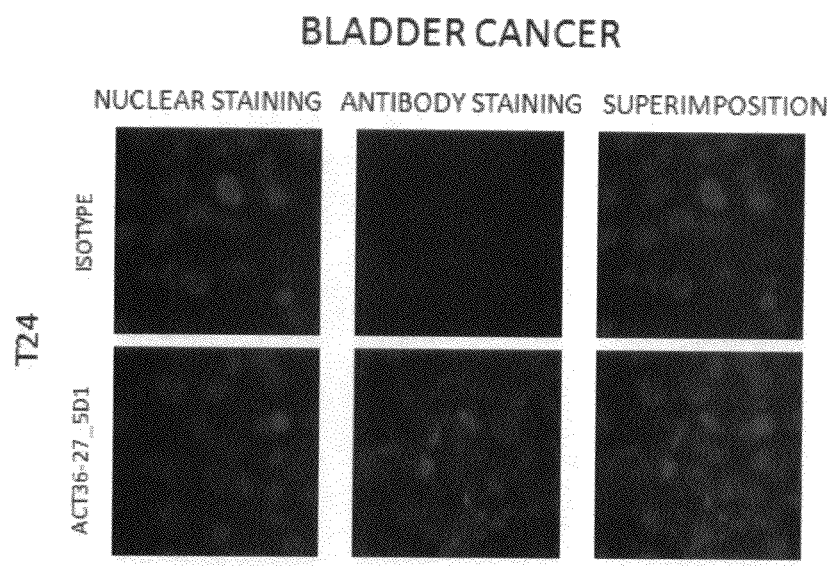
FIG. 3B shows graphs illustrating the result of analyzing, by cell staining, the reactivity between the ACT36-27_5D1 antibody and the surfaces of cultured cancer cells. As the cancer cell line, the bladder cancer cell line (T24) was used.
Figure 3C:
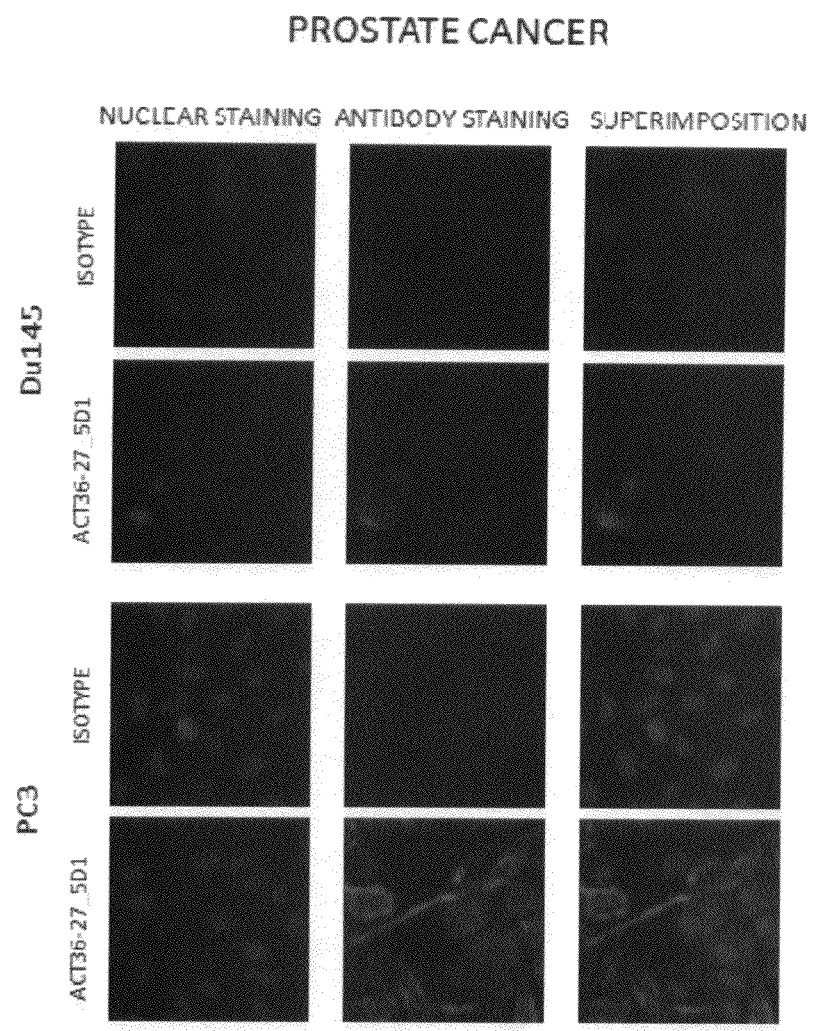
FIG. 3C shows graphs illustrating the result of analyzing, by cell staining, the reactivity between the ACT36-27_5D1 antibody and the surfaces of the various cultured cancer cells. As the cancer cell lines, the prostate cancer cell lines (Du145, PC3) were used.
Figure 3D:
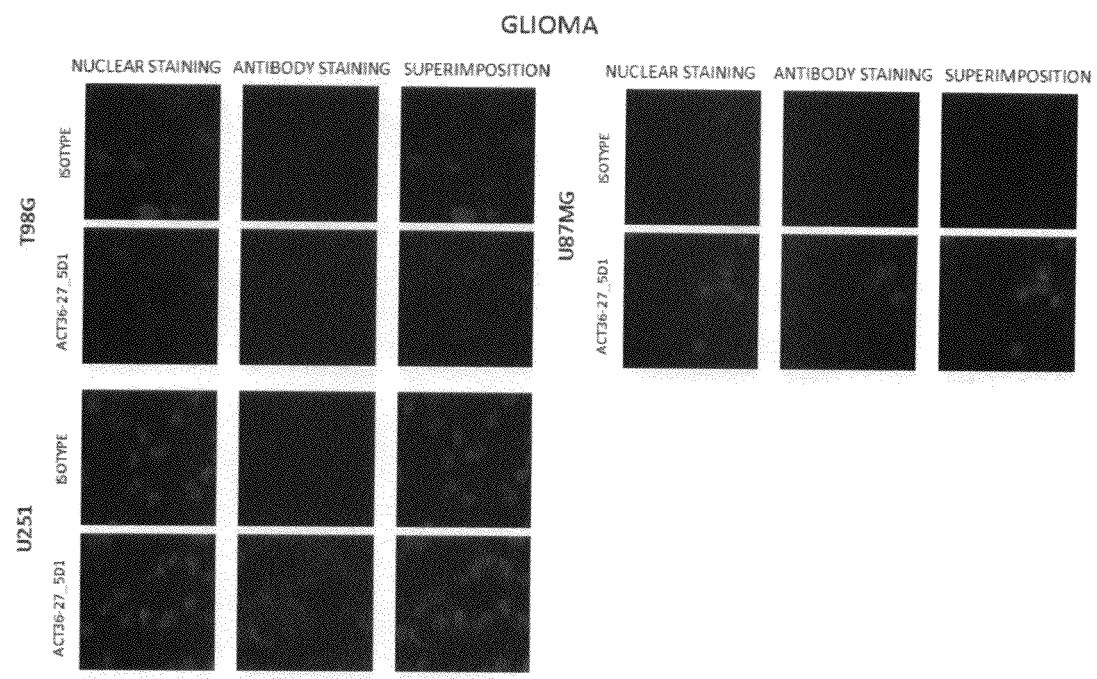
FIG. 3D shows graphs illustrating the result of analyzing, by cell staining, the reactivity between the ACT36-27_5D1 antibody and the surfaces of the various cultured cancer cells. As the cancer cell lines, the glioma cell lines (T98G, U251, U87MG) were used.
Figure 3E:
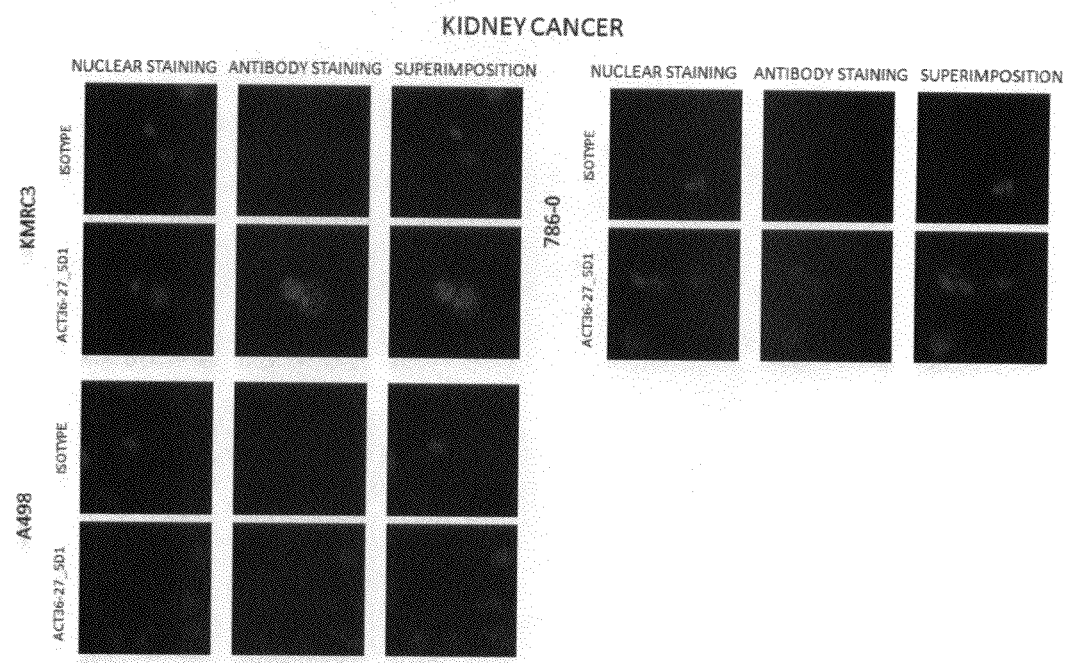
FIG. 3E shows graphs illustrating the result of analyzing, by cell staining, the reactivity between the ACT36-27_5D1 antibody and the surfaces of various cultured cancer cells. As the cancer cell lines, kidney cancer cell lines (KMRC3, 786-0, A498) were used.
Figure 3F:
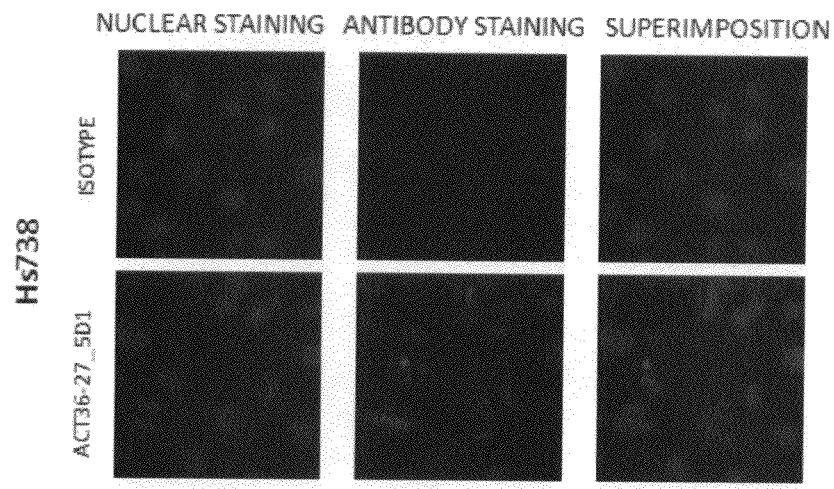
FIG. 3F shows graphs illustrating the result of analyzing, by cell staining, the reactivity between the ACT36-27_5D1 antibody and a mixture of fetal gastric and intestinal cells.

When at 80% confluency, cancer cells to be stained were detached from the culture plate using Cell Dissociation Buffer (GIBCO, 13151-014) and collected. In each of 0.5% BSA and 2 mM EDTA/PBS (wash buffers shown in Example 4), 100 µl of 1×10$^5$ cells thus collected were suspended, and then dispensed into a 96-well plate (BD Falcon, 353911). Thereafter, the reactivity between the cancer cells and the antibody was analyzed using a flow cytometer by the same method as in Example 4 (FIG. 2).

As the cancer cells which were subjected to the analysis on the reactivity with the ACT36-27_5D1 antibody, gastric cancer cell lines (GCIY, MKN1), a bladder cancer cell line (T24), prostate cancer cell lines (Du145, PC3), and glioma cell lines (T98G, U251, U87MG) were used. As a result, the ACT36-275D1 antibody significantly reacted with all the subjected cancer cells in comparison with the isotype control antibody.

Example 6

Cell Staining of Cancer Cells

The reactivity between the ACT36-27_5D1 antibody and various cancer cells was analyzed by cell staining. In a black 96-well plate (BD Falcon, 353219), 1×10$^4$ cancer cells to be stained were suspended and seeded in 100 µl of a medium, and cultured for 24 hours. As the medium for the various cancer cells of cancers, a DMEM medium (SIGMA) containing 10% FBS (Equitech) and 1% penicillin/streptomycin solution (GIBCO Penicillin-streptomycin liquid, 15140122, hereinafter abbreviated as "P/S") which were subjected to an inactivation treatment was used. In this Example, as a wash buffer, a buffer containing 25 mM HEPES (pH7.4), 120 mM NaCl, 4.8 mM KCl, 1.2 mM MgSO$_4$, and 1.3 mM CaCl$_2$ was used.

When only the cell surface was stained, 50 µl of the wash buffer in which 2 µg/ml of the hybridoma culture supernatant or the purified antibody was dissolved was added to the cells obtained by removing a culture supernatant by centrifugation at 700×g for 2 minutes. As negative controls of the ACT36-27_5D1 antibody, solutions to each of which 50 µl of a wash buffer dissolving mouse IgG1 (BioLegend, 400412), mouse IgG2a (BioLegend, 400224), or mouse IgG2b (BioLegend, 400324) at a concentration of 2 µg/ml were used. Each antibody was reacted at room temperature for 30 minutes, followed by centrifugation at 700×g for 2 minutes. A supernatant was removed. Further, 100 µl of a wash buffer was added, followed by centrifugation at 700×g for 2 minutes again. A supernatant was removed. Then, the cells were washed.

After the washing, 50 µl of Goat anti-mouse IgG, F(ab') 2-PE (Beckman Coulter, IM0855) diluted 200-fold with a wash buffer and further diluted 2,000-fold with 10 mg/ml of Hoechst 33342 (Invitrogen, H1399) was added as a secondary antibody for detection and as a nuclear staining agent to the cells, and reacted at room temperature for 30 minutes in the dark. Then, washing was performed twice in the above-described manner. After 100 µl of a wash buffer was added, cell staining was observed using In Cell Analyzer 1000 (GE healthcare Life Sciences).

When the cell surface and the cell interior were stained, a supernatant of the cell culture liquid was removed by centrifugation. The resultant cells were washed with 100 µl of a wash buffer once in the above-described manner. Then, 50 µl of 4% Paraformaldehyde Phosphate Buffer Solution (Wako, 161-20141) was added, and reacted at room temperature for minutes to fix cells. Subsequently, washing was performed twice with 100 µl of a wash buffer. Next, 100 µl of a wash buffer containing 0.1% Triton X-100 was added, and reacted at room temperature for 10 minutes to increase the permeability of the cell membrane. Thereafter, washing was performed twice with 100 µl of a wash buffer. After that, staining and analysis were conducted in the same manner as the method of staining only the cell surface.

In observing the cells, the nucleus stained with Hoechst 33342 was set as the position of the cell. Fluorescence from PE was measured to examine the presence or absence of staining by the antibody. As an index of the staining intensity by the antibody, a ratio of the cells having at least a certain level of PE fluorescence intensity was analyzed using Developer (GE healthcare Life Sciences) that is analysis software accompanying In Cell Analyzer.

Figure 4:
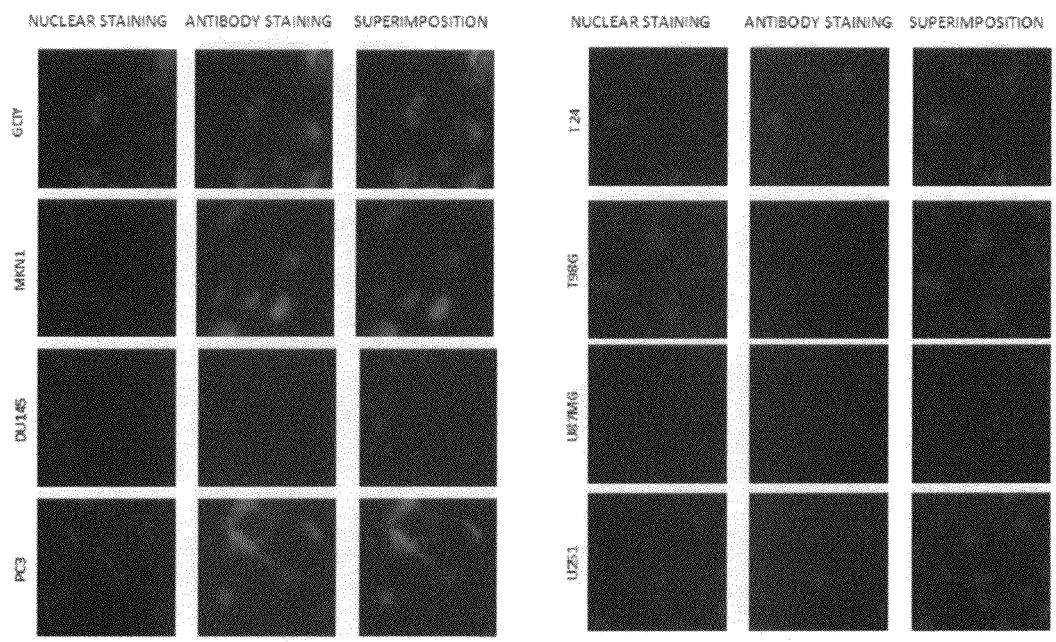
FIG. 4 shows graphs illustrating the result of staining the surfaces and the cell interiors of the various cultured cancer cells by the ACT36-27_5D1 antibody. As the target cancer cell lines, the gastric cancer cell lines (GCIY, MKN1), the bladder cancer cell line (T24), the prostate cancer cell lines (Du145, PC3), and the glioma cell lines (T98G, U251, U87MG) were used. The graphs on the left show nuclear staining images by using Hoechst 33342. The graphs in the center show staining images by the antibody. The graphs on the right show superimposed images of the nuclear staining images by using Hoechst 33342 on the staining images by the antibody.

The cell surfaces of the various cancer cell lines used in Example 5, kidney cancer cell lines (KMRC3, 786-0, A498), and a mixture of fetal gastric and intestinal cells were subjected to cell staining by the anti-ACT36-27_5D1. The reactions were observed in the gastric cancer cell lines (GCIY, MKN1), the prostate cancer cell line (PC3), and the bladder cancer cell line (T24) (FIG. 3). When the cell surfaces and the cell interiors of the various cancer cells lines used in Example 5 were stained, the staining intensities were different, but the reactions were observed in the gastric cancer cell lines (GCIY, MKN1), the prostate cancer cell line (PC3), and the bladder cancer cell line (T24) (FIG. 4). This suggests that these cancer cells expressed PODXL2 with which the ACT36-27_5D1 antibody reacted.

Example 7

Effect of Anti-ACT36-27_5D1 Monoclonal Antibody on Growth of Cancer Cells (MTT)

The influence of the ACT36-27_5D1 antibody on growth of the cancer cells was analyzed using an MTT assay. As a medium for various cancer cells, a RPMI1640 medium (WAKO) containing 10% FBS (Equitech, the same shall apply hereinafter) and 1% P/S which were subjected to an inactivation treatment was used for a prostate cancer cell line AsPC1, while a DMEM medium (SIGMA) containing 10% FBS and 1% P/S solution which were subjected to an inactivation treatment was used for the other cancer cells. As a medium for the hybridoma producing the target antibody, a RPMI medium (Wako) containing required amounts of HT (Sigma-Aldrich H0137, HT media supplement (50×) Hybri-Max), 15% FBS, and 1% P/S solution was used.

In addition, as a control, a mouse isotype control mixture solution in which 1 μl of each of Mouse IgG1 (BECKMAN COULTER 731581), IgG2a (MBL M076-3), IgG2b (MBL M077-3), and IgG3 (MBL M078-3) was dissolved in 1 ml of the hybridoma medium was used.

The experiments were conducted in three wells of the antibody culture supernatant per experiment. Each line of the various cancer cells was seeded into a 96-well plate (IWAKI) in such a manner that $2 \times 10^3$ cells were in 100 μl of the medium per well, followed by incubation under a condition of 5% $CO_2$ at 37° C. for 24 hours.

To the 96-well plate after the incubation, the culture supernatant containing the ACT36-27_5D1 antibody or the mouse isotype control was added by 100 μl per well, followed by incubation for 72 hours. A culture supernatant was removed by centrifugation. To the resultant cells, 100 μl of a 5% WST-1 solution (vol./vol., Roche 11 644 807 001) adjusted by dissolving a fresh cancer cell medium therein was added, followed by incubation for 1 to 4 hours. The color of the WST-1 was determined every hour with Microplate Reader (BIO-RAD).

Figure 5A:
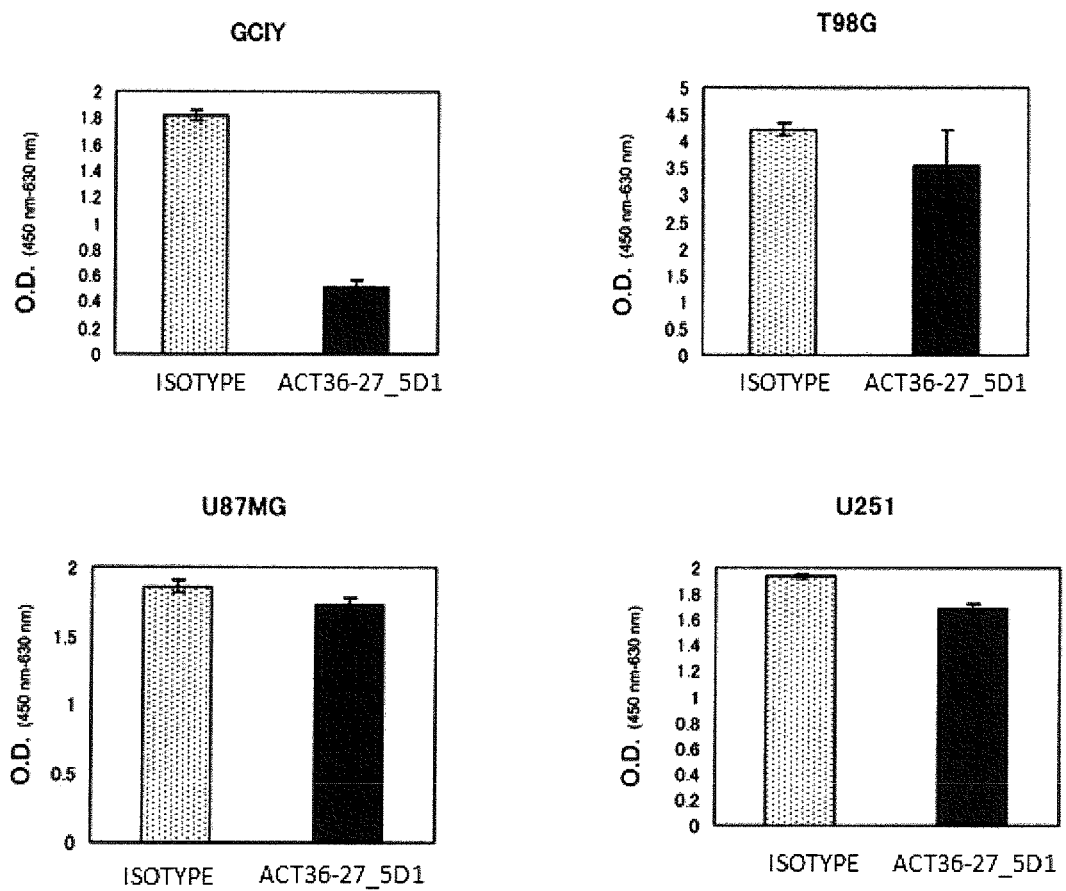
FIG. 5A shows graphs illustrating the result of analyzing, by an MTT assay, an influence of the anti-ACT36-27_5D1 monoclonal antibody on growth of the cancer cell. The vertical axis represents O.D. (O.D. 450 nm to O.D. 630 nm) values 3 hours after WST-1 was added. As the target cancer cell lines, the gastric cancer cell line (GCIY) and the glioma cell lines (T98G, U251, U87MG) were used.
Figure 5B:
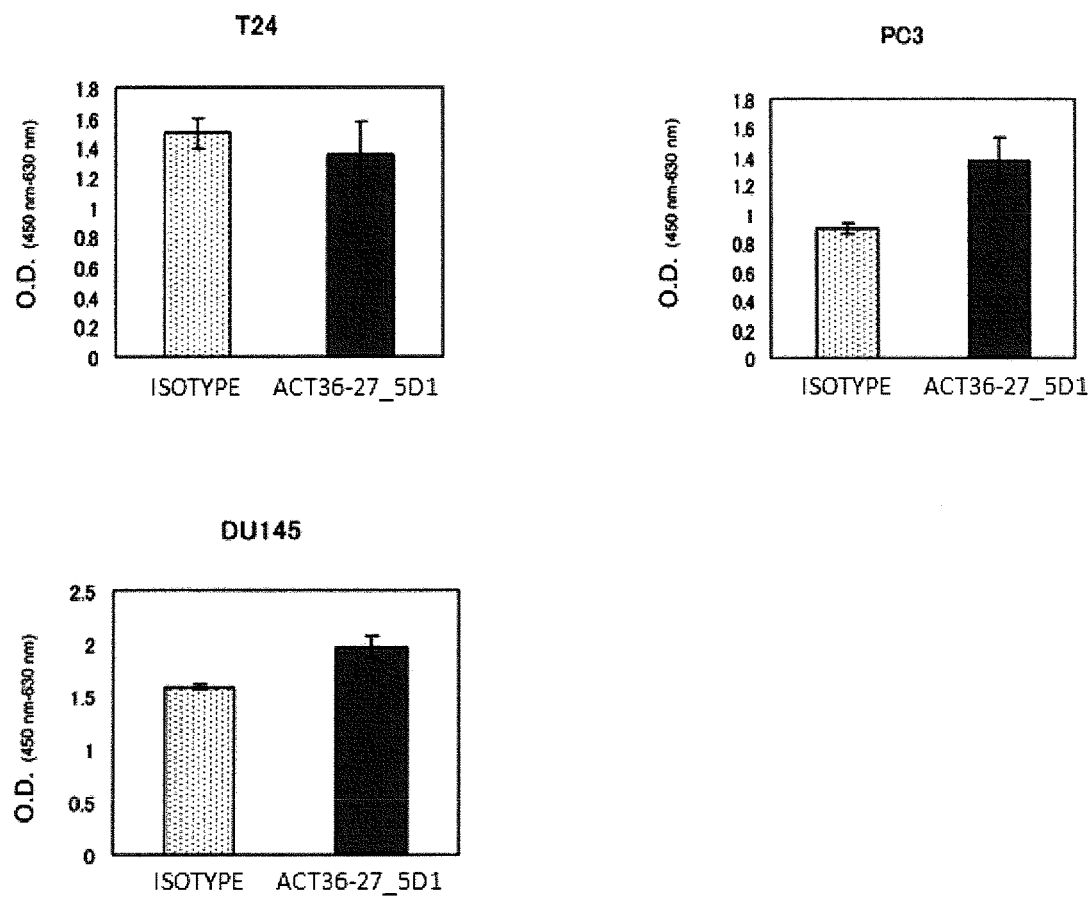
FIG. 5B shows graphs illustrating the result of analyzing, by the MTT assay, an influence of the anti-ACT36-27_5D1 monoclonal antibody on growth of the cancer cells. The vertical axis represents O.D. (O.D. 450 nm to O.D. 630 nm) values 3 hours after WST-1 was added. As the target cancer cell lines, the bladder cancer cell line (T24) and the prostate cancer cell lines (Du145, PC3) were used.

FIG. 5 shows the determination result in a graph form. In this data, the color of WST-1 after 3 hours is represented by the O.D. value (O.D. 450 nm to O.D. 630 nm). In the MTT assay, the effect of the ACT36-27_5D1 antibody suppressing the cancer cell growth was significantly demonstrated on the GCIY cells. The cell growth was suppressed to approximately 28% of that of the isotype control.

Example 8

Effect of Antibody Administered to Tumor-Bearing Mouse Model through Caudal Vein The in vivo effect of the ACT36-27_5D1 antibody was examined using a tumor-bearing mouse model.

A cell suspension was injected subcutaneously at the back of the necks of 6-week-old male SCID mice (5 weeks old when purchased from CLEA Japan, Inc.) in such a manner that the GCIY cells were $5 \times 10^6$/0.2 ml saline/mouse individual. At 3 weeks after the injection, the size of an engrafted tumor was measured. The tumor-bearing mice were grouped into three groups of a control group, a positive control group, and an anti-ACT36-27_5D1 antibody group in such a manner that an average tumor volume of each group including five mice was approximately $55 \pm 5$ mm$^3$.

Into each of the groups, a sample was administered through the caudal vein of the tumor-bearing mouse from 3 weeks after the cell injection. A saline (Otsuka normal saline) was administered to the control group. Taxotere (600 μg for each mouse individual, sanofi-aventis K.K.) was administered to the positive control group. The anti-ACT36-27_5D1 monoclonal antibody (10 mg/kg) was administered to the antibody administered group. The sample was administered through the caudal vein once a week (consecutively for 3 weeks, 3 times in total). Moreover, immediately before each administration, the weight measurement and the tumor measurement were conducted. For the weight measurement, an animal balance was used. For the tumor measurement, the major axis and the minor axis were measured with a digimatic caliper, and the tumor volume was calculated according to the following formula.

$$\text{Tumor volume (mm}^3\text{)}=0.5 \times \text{major axis} \times \text{minor axis} \times \text{minor axis}$$

Figure 6:
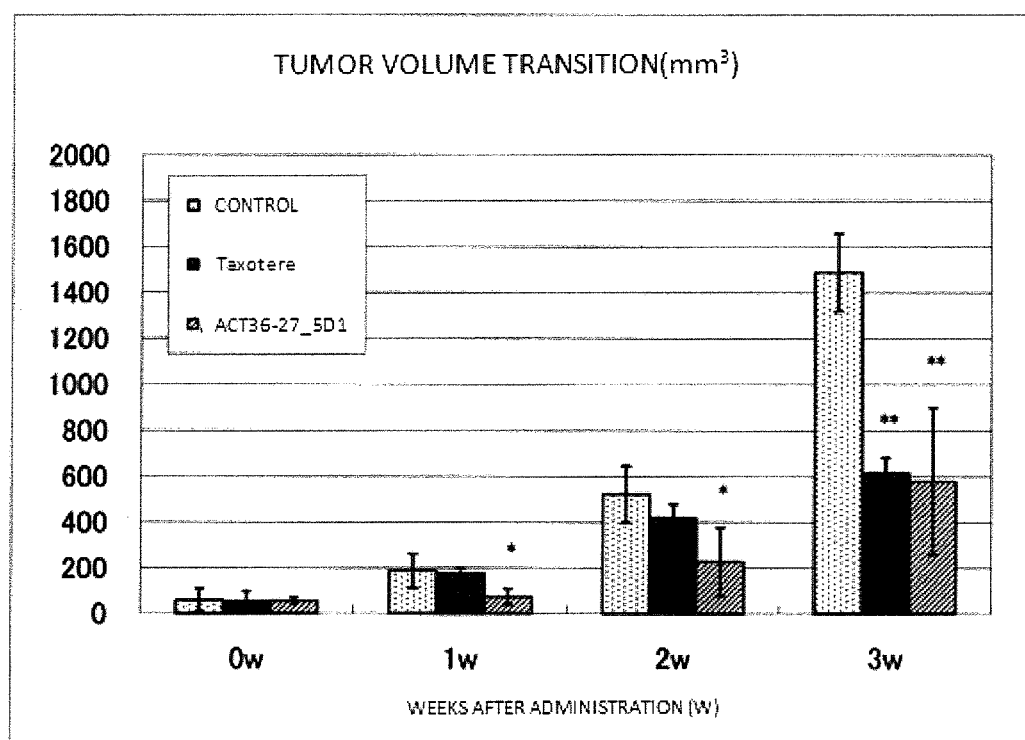
FIG. 6 shows a graph illustrating the tumor volume transition of a tumor-bearing mouse model to which the ACT36-27_5D1 antibody was administered. A saline was used as a control, and Taxotere was used as a positive control.

The tumor volume data was compared with those of the control groups, and the anti-tumor effect over time was examined. FIG. 6 shows the result.

In the control group, the tumor enlarged over time. When the experiment was finished 3 weeks after the start of the administration, the tumor volume was approximately 25 times larger than that at the time of the start. In contrast, in the group to which Taxotere was administered, tumor growth suppression was observed from 2 weeks after the administration was started. At 3 weeks when the experiment was finished, the tumor volume was just of the order of approximately 11 times that at the time when the experiment was started. Hence, tumor volume suppression to approximately 59% of that of the control group was observed. Moreover, in the group to which the ACT36-27_5D1 antibody was administered, the tumor growth suppression effect was observed in comparison with the control group from 1 week after the administration was started. The tumor growth suppression effect was further enhanced at the time when the experiment was finished. The tumor volume was just of the order of approximately 10 times that at the time when the administration was started. Hence, the tumor volume was suppressed to approximately 61% of that of the control group.

Figure 7:
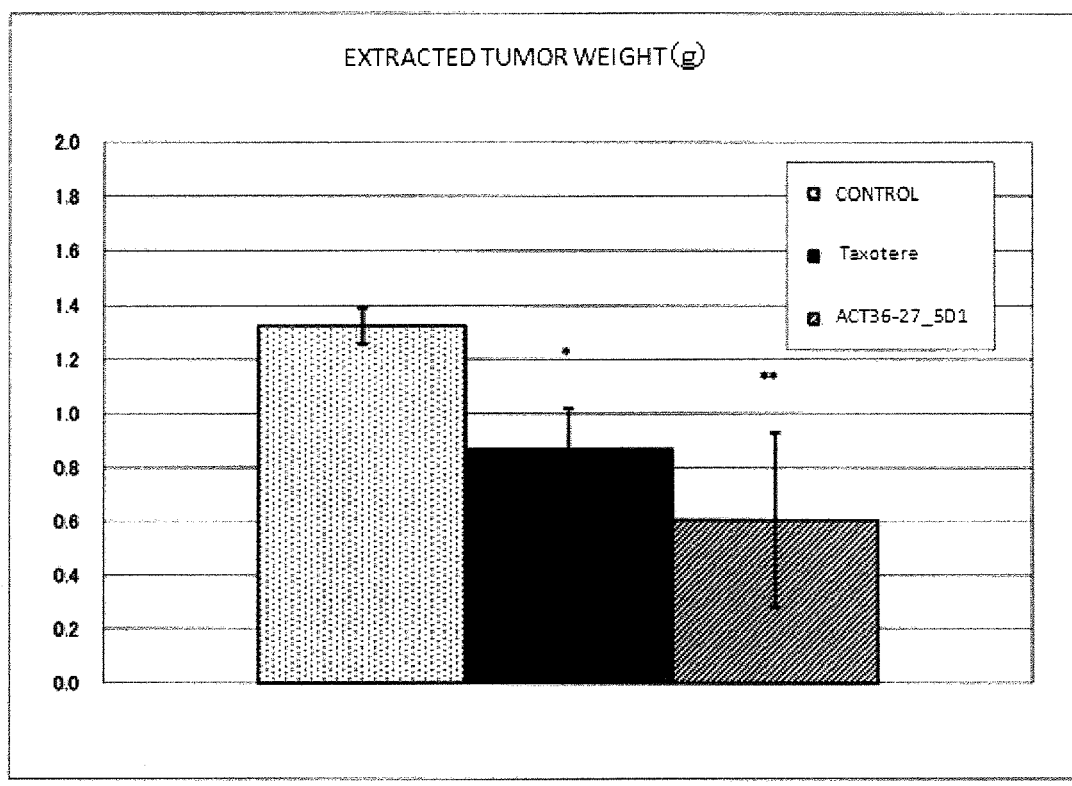
FIG. 7 shows a graph illustrating the extracted tumor weight of the tumor-bearing mouse model 3 weeks after the ACT36-27_5D1 antibody was administered. The saline was used as the control, and Taxotere was used as the positive control.

A necropsy was performed 3 weeks after the administration of each sample was started. After the tumor-bearing mouse was killed under anesthesia with ether, a tumor under the skin at the back of the neck was extracted, and the weight was measured. The tumor weights were compared among the groups. FIG. 7 shows the result. The extracted tumor weights were: 1.33 g for the control group, 0.87 g for the positive control group, and 0.61 g for the ACT36-27_5D1 antibody group. In the group to which the ACT36-27_5D1 antibody was administered, the extracted tumor weight was of the order of approximately 54% smaller than that the control group. Hence, a stronger tumor growth suppression effect was observed than that the positive control group.

Figure 8:
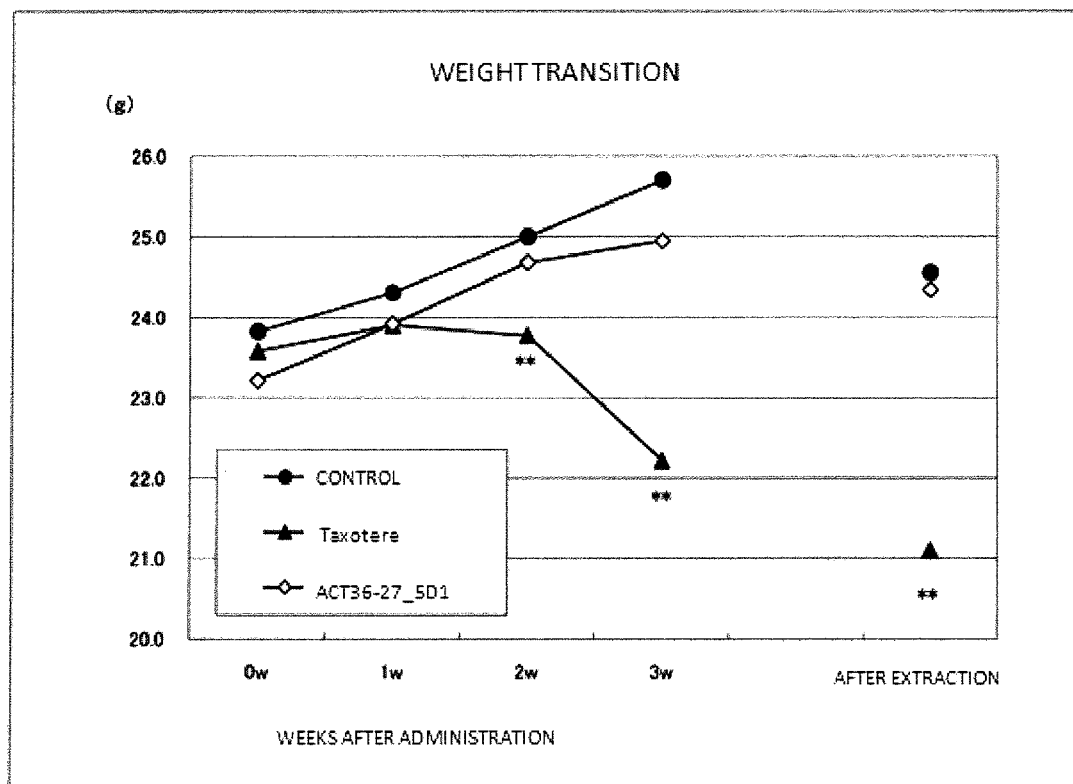
FIG. 8 shows a graph illustrating the weight transition of the tumor-bearing mouse model to which the ACT36-27_5D1 antibody was administered. The saline was used as the control, and Taxotere was used as the positive control.

FIG. 8 shows the weight measurement result. Regarding the weight transition, in the positive control group, significant weight reduction was observed from 2 weeks after the administration was started. Meanwhile, in the ACT36-27_5D1 antibody group, weight reduction was not observed. Regarding weight calculated by subtracting the tumor weight from the weight at the time of the necropsy, the weight reduction in the positive control group was obvious, while weight increase was obtained in the ACT36-27_5D1 antibody group.

Example 9

Antibody Variable Region-Determination Method

To clarify the gene sequence of variable regions of the ACT36-27_5D1 antibody, 2×10$^6$ cells of the hybridoma cells producing the ACT36-27_5D1 antibody were suspended in 1 ml of Trizol (invitrogen, #15596-026) and left for 5 minutes, and 200 µl of chloroform was added thereto, followed by suspension for 15 seconds and centrifugation at 12,000×g for 15 minutes to obtain a supernatant. This supernatant and 500 µl of isopropanol were mixed together, followed by centrifugation at 12,000×g for 10 minutes. The resulting pellets were washed with 80% ethanol, and 40 µg of total RNAs were obtained. A total amount thereof was dissolved in 20 µl of water. A solution containing 5 µg of the total RNAs among this was used. Using SuperScript™ Choice System (invitorgen, #18090-019), double-stranded cDNAs were prepared from the total RNAs. The obtained double-stranded cDNAs were ethanol precipitate. Then, using Ligation High (TOYOBO, #LGK-201), the 5'-end and the 3'-end of the double-stranded cDNAs were ligated, 1 µl of which were used as a template to perform PCR. Primers used were designed for constant regions of a heavy chain and a light chain. The primers had sequences as follows.

```
                                      (SEQ ID NO: 18)
    Heavy chain 5' gtccacgaggtgctgcacaat (SEQ ID NO: 19)
    Heavy chain 3' gtcactggctcagggaaataacc (SEQ ID NO: 20)
    Light chain 5' aagatggatacagttggtgc (SEQ ID NO: 21)
    Light chain 3' tgtcaagagcttcaacagga
```

The PCR products were electrophoresed on a 1.5% gel, and then cut out for purification. Using the purified DNAs, sequencing was performed. As to the light chain, the sequencing was performed after the purified DNAs were cloned. The base sequence of the variable region of the light chain thus determined is shown in SEQ ID NO: 9, and the amino acid sequence thereof is shown in SEQ ID NO: 10. The base sequence of the variable region of the heavy chain is shown in SEQ ID NO: 11, and the amino acid sequence thereof is shown in SEQ ID NO: 12.

In addition, these amino acid sequences of the variable regions were numbered utilizing the sequence analysis in the site "Andrew C. R. Martin's Bioinformatics Group" of UCL (bioinf.org.uk/abysis/tools/analyze.cgi). A CDR region was identified according to the standard described in "Table of CDR Definitions" (bioinf.org.uk/abs/#kabatnum). FIG. 9 shows the result of CDR prediction and signal sequences of the light chain and the heavy chain. Moreover, the amino acid sequences of CDR1, CDR2, and CDR3 of the light chain are shown in SEQ ID NOs: 3 to 5. The amino acid sequences of CDR1, CDR2, and CDR3 of the heavy chain are shown in SEQ ID NOs: 6 to 8.

Example 10

Preparation of Target Factor Region-Expressing Cells for Epitope Analysis and Epitope Analysis To specify the epitope of the ACT36-27_5D1 antibody, Ba/F3 cells expressing PODXL2 peptides of various chain lengths were prepared, and the reactivity with the antibody was evaluated.

In total, 14 types of peptides were prepared: PODXL2, positions 1 to 428 (indicating positions of amino acids from the N terminal. The same shall apply hereinafter) that corresponds to the full-length extracellular region, peptides which are consecutively shortened by cutting a C-terminus portion in 10-amino acid length such as positions 1 to 420, positions 1 to 410, positions 1 to 400, . . . , to positions 1 to 300. These were peptides to be analyzed. Using DNAs having the following sequences as primers, and using PrimeSTAR MAX DNA polymerase (TaKaRa #R045A) as a polymerase, 14 types of genes were isolated with a template of the cDNA library on which the GCIY signal sequence trap method described in Example 1 was executed.

```
The forward primer (common to the 14 types
of genes) is as follow.
                                      (SEQ ID NO: 22)
ccggaattcagaggcgacgacacgatgcg The reverse primers (each value added to
R means the chain length of a peptide
encoded by an amplification product)
is as follows.
                                      (SEQ ID NO: 23)
R300: ttttccttttgcggccgcgagaaggtgttttggggtatc (SEQ ID NO: 24)
R310: ttttccttttgcggccgctgcccagttactctcatgag (SEQID NO: 25)
R320: ttttccttttgcggccgcctgtgtctgtgtctcaacatc (SEQ ID NO: 26)
R330: ttttccttttgcggccgctgtgaagttcaggacgagc (SEQ ID NO: 27)
R340: ttttccttttgcggccgccgaagcgcccctgcacag (SEQ ID NO: 28)
R350: ttttccttttgcggccgctcggcatatcagtgagatc (SEQ ID NO: 29)
R360: ttttccttttgcggccgcttgggccgggttgaaggtgg (SEQ ID NO: 30)
R370: ttttccttttgcggccgcaacagatgccagccgtatgc (SEQ ID NO: 31)
R380: ttttccttttgcggccgcttctttgacgaccacggtc (SEQ ID NO: 32)
R390: ttttccttttgcggccgccttggcagggagcttagtg (SEQ ID NO: 33)
R400: ttttccttttgcggccgcccatttgtccttcagccgc (SEQ ID NO: 34)
R410: ttttccttttgcggccgcgtcactgaccccctgcctcc (SEQ ID NO: 35)
R420: ttttccttttgcggccgcctccggtggcccctggtccc (SEQ ID NO: 36)
R428: ttttccttttgcggccgcgatgaggggcatgctgaagc
```

The obtained PCR products were electrophoresed on a 1% agarose gel, and then cut out and purified, followed by restriction enzyme treatment with EcoRI and NotI. The pMX-SST was also treated with the EcoRI and NotI restriction enzymes, and cut out and purified. Further, both were treated with Ligation High (TOYOBO, #LGK-201), followed by the same treatment as in Example 2 (i.e., after the transformation of *Escherichia coli*). A LB agarose plate containing 50 μg of ampicillin was plated with the transformed *Escherichia coli*. PCR was performed in such a manner that the inserted portions from colonies obtained by culturing at 37° C. overnight were contained. Whether the pMX-SST vector contained a desired sequence was checked by sequencing. As PCR primers for the sequencing, the following oligonucleotides were used.

```
SST3'-T7
                                                (SEQ ID NO: 37)
5'-TAATACGACTCACTATAGGGCGCGCAGCTGTAAACGGTAG-3'

SST5'-T3
                                                (SEQ ID NO: 38)
5'-ATTAACCCTCACTAAAGGGAGGGGGTGGACCATCCTCTA-3'
```

Figure 10:
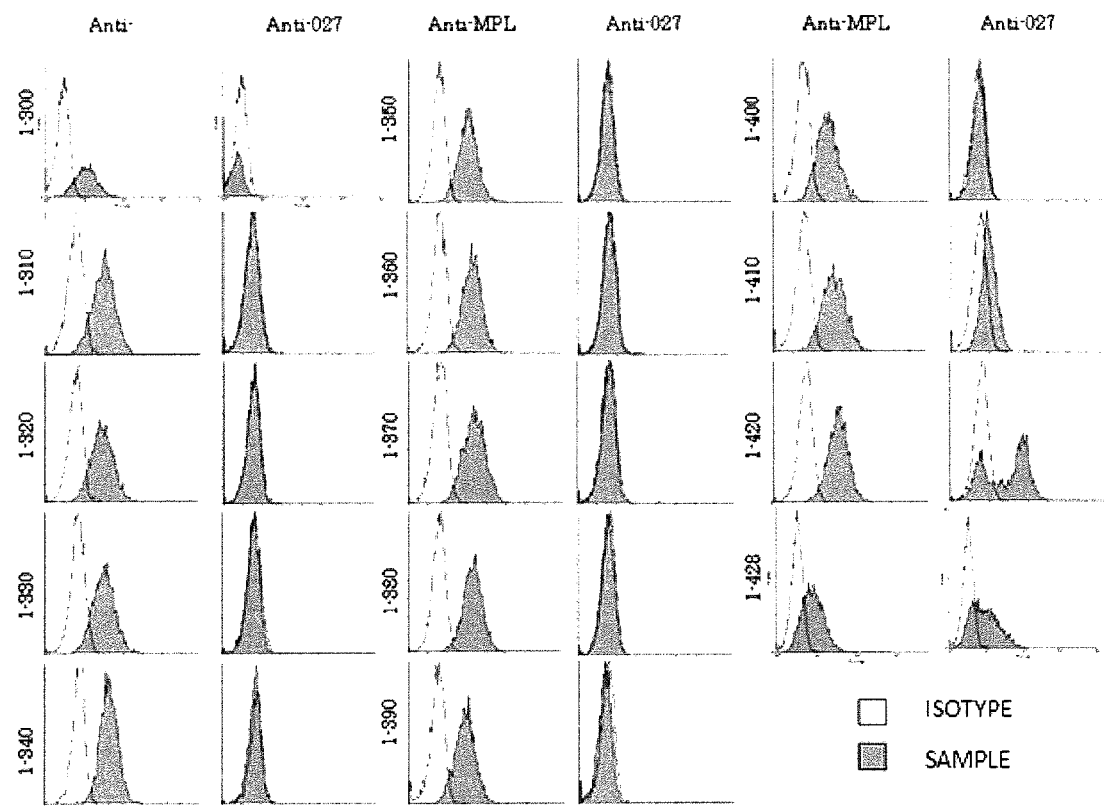
FIG. 10 shows graphs illustrating the reactivity between the ACT36-27_5D1 antibody and transfectant Ba/F3 cells expressing PODXL2 genes of various lengths. A flow cytometer was used to analyze the reactivity of the ACT36-27_5D1 antibody and a control MPL antibody with the Ba/F3 cells expressing multiple peptides having different chain lengths and containing the N terminal of an antigen PODXL2 molecule. A filled histogram part in each flow cytometer data illustrates the reaction with the antibody against each PODXL2 molecule, while a white histogram part illustrates the reaction with mouse IgG2a used as a control.

Thereafter, by the same method as in Example 1 (4) (the virus packaging and thereafter), Ba/F3 cells containing the PODXL2 gene sequences of various chain lengths were prepared. Further, by the same method as in Example 4, the reactivity between the ACT36-27_5D1 antibody and the Ba/F3 cells expressing the PODXL2 molecules of various chain lengths was analyzed by a flow cytometer (FIG. 10). As a result, the ACT36-27_5D1 antibody did not show the reactivity with the clones expressing the PODXL2 molecules at the positions 1 to 400 or less, but showed the reactivity with the clones expressing the regions at positions 1 to 410, positions 1 to 420, and positions 1 to 428. From the above, it was revealed that the epitope of the antibody was contained between positions 400 to 428 of the PODXL2 molecule.

Comparative Example 1

By the method described in Example 3, four clones, other than ACT36-27_5D1, producing the anti-PODXL2 antibody were obtained: "ACT36-27_7G11K," "ACT36-27_2C12E1B," "ACT36-27_3D10B," and "ACT36-27_7E2B." The isotypes of the antibody produced were IgG2a/κ for "ACT36-27_7G11K" and "ACT36-27_2C12E1B," and IgG1/κ for "ACT36-27_3D10B" and "ACT36-27_7E2B." By the method described in Example 7, the MTT assay was conducted on the monoclonal antibodies produced by these clones. As a result, none demonstrated cancer cell growth suppression effect. Moreover, the epitope analysis was conducted by the method described in Example 10. As a result, it was revealed that all had the epitope contained in the amino acid sequence between positions 1 to 310.

As described above, all of the antibodies recognizing the amino acid sequence between positions 1 to 310 of PODXL2 did not demonstrate cancer cell growth suppression effect, while the ACT36-27_5D1 antibody recognizing the amino acid sequence between positions 400 to 428 demonstrated excellent cancer cell growth suppression effects in vitro and in vivo. This suggests that in order for the anti-PODXL2 antibody to demonstrate the cancer cell growth suppression effect, the anti-PODXL2 antibody preferably recognizes the amino acid sequence other than positions 1 to 310 (i.e., between positions 311 and 428), particularly the amino acid sequence between positions 400 and 428.

INDUSTRIAL APPLICABILITY

Since having an excellent anti-cancer activity, a monoclonal antibody of the present invention can be used for treatment or prevention of cancer. Particularly, the monoclonal antibody of the present invention demonstrates a strong cell growth suppression effect on gastric cancer and also demonstrates an effect of suppressing reduction in target weight. The monoclonal antibody of the present invention is considered to have an excellent effect on scirrhous gastric cancer which is highly malignant and difficult to treat so far, and thus extremely useful in medical treatment. Moreover, since binding to a surface of a cancer cell, the monoclonal antibody of the present invention is applicable also to cancer diagnosis, and detection, screening, and the like of cancer cells.

---

The invention claimed is:

1. An antibody or epitope binding fragments thereof, capable of binding an epitope of human-derived PODXL2 protein, wherein the epitope is contained between amino acid residues corresponding to residues 311 and 428 of SEQ ID NO:2 and wherein the antibody has an anti-cancer activity.

2. The antibody and epitope binding fragments thereof according to claim 1, which binds to an epitope contained between amino acid residues corresponding to residues 400 and 428 of SEQ ID NO:2.

3. The antibody or epitope binding fragments thereof according to claim 1, wherein the cancer is gastric cancer.

4. The antibody or epitope binding fragments thereof according to claim 1, comprising:
    a light chain variable region comprising amino acid sequences of SEQ ID NOs: 3 to 5; and
    a heavy chain variable region comprising amino acid sequences of SEQ ID NOs: 6 to 8.

5. The antibody or epitope binding fragments thereof according to claim 1, comprising:

a light chain variable region comprising an amino acid sequence of SEQ ID NO: 10; and a heavy chain variable region comprising an amino acid sequence of SEQ ID NO: 12.

6. The antibody or epitope binding fragment thereof comprising the amino acid sequences of SEQ ID NOs: 10 and 12 of the antibody according to claim 5, from at least one of which a signal sequence is removed, and having an equivalent activity to that of the antibody according to claim 5.

7. A peptide comprising any one of a light chain and a variable region thereof, of the antibody according to claim 1 comprising amino acid sequences of SEQ ID NOs: 3 to 5.

8. The peptide according to claim 7, comprising any one of:
an amino acid sequence of SEQ ID NO: 10; and
an amino acid sequence of SEQ ID NO: 10 from which a signal sequence is removed.

9. A peptide comprising any one of a heavy chain and a variable region thereof, of the antibody according to claim 1 comprising amino acid sequences of SEQ ID NOs: 6 to 8.

10. The peptide according to claim 9, comprising any one of:
an amino acid sequence of SEQ ID NO: 12; and
an amino acid sequence of SEQ ID NO: 12 from which a signal sequence is removed.

11. A hybridoma which produces the antibody according to claim 1.

12. An antibody produced by the hybridoma according to claim 11.

13. An anti-cancer agent comprising the antibody according to claim 1 as an active ingredient.

14. The anti-cancer agent according to claim 13, wherein the cancer is gastric cancer.

* * * * *

UNITED STATES PATENT AND TRADEMARK OFFICE
CERTIFICATE OF CORRECTION

PATENT NO. : 8,828,387 B2  
APPLICATION NO. : 13/382468  
DATED : September 9, 2014  
INVENTOR(S) : Masunori Kajikawa et al.

Page 1 of 1

It is certified that error appears in the above-identified patent and that said Letters Patent is hereby corrected as shown below:

In The Claims

Column 45, line 64 (Claim 2), "The antibody and epitope binding fragments thereof", should be -- The antibody or epitope binding fragments thereof --.

Signed and Sealed this
Seventeenth Day of March, 2015

Michelle K. Lee
*Director of the United States Patent and Trademark Office*

SEQUENCE LISTING

```
<160> NUMBER OF SEQ ID NOS: 38

<210> SEQ ID NO 1
<211> LENGTH: 1581
<212> TYPE: DNA
<213> ORGANISM: Homo sapiens
<220> FEATURE:
<221> NAME/KEY: CDS
<222> LOCATION: (1)..(1578)

<400> SEQUENCE: 1 atg cgc tgc gcg ctg gcg ctc tcg gcg ctg ctg cta ctg ttg tca acg      48
Met Arg Cys Ala Leu Ala Leu Ser Ala Leu Leu Leu Leu Leu Ser Thr
1               5                   10                  15 ccg ccg ctg ctg ccg tcg tcg ccg tcg ccg tcg ccg tcg ccc tcc cag      96
Pro Pro Leu Leu Pro Ser Ser Pro Ser Pro Ser Pro Ser Pro Ser Gln
            20                  25                  30 aat gca acc cag act act acg gac tca tct aac aaa aca gca ccg act     144
Asn Ala Thr Gln Thr Thr Thr Asp Ser Ser Asn Lys Thr Ala Pro Thr
        35                  40                  45 cca gca tcc agt gtc acc atc atg gct aca gat aca gcc cag cag agc     192
Pro Ala Ser Ser Val Thr Ile Met Ala Thr Asp Thr Ala Gln Gln Ser
    50                  55                  60
```

```
aca gtc ccc act tcc aag gcc aac gaa atc ttg gcc tcg gtc aag gcg    240
Thr Val Pro Thr Ser Lys Ala Asn Glu Ile Leu Ala Ser Val Lys Ala
 65                  70                  75                  80 acc acc ctt ggt gta tcc agt gac tca ccg ggg act aca acc ctg gct    288
Thr Thr Leu Gly Val Ser Ser Asp Ser Pro Gly Thr Thr Thr Leu Ala
                 85                  90                  95 cag caa gtc tca ggc cca gtc aac act acc gtg gct aga gga ggc ggc    336
Gln Gln Val Ser Gly Pro Val Asn Thr Thr Val Ala Arg Gly Gly Gly
            100                 105                 110 tca ggc aac cct act acc acc atc gag agc ccc aag agc aca aaa agt    384
Ser Gly Asn Pro Thr Thr Thr Ile Glu Ser Pro Lys Ser Thr Lys Ser
        115                 120                 125 gca gac acc act aca gtt gca acc tcc aca gcc aca gct aaa cct aac    432
Ala Asp Thr Thr Thr Val Ala Thr Ser Thr Ala Thr Ala Lys Pro Asn
    130                 135                 140 acc aca agc agc cag aat gga gca gaa gat aca aca aac tct ggg ggg    480
Thr Thr Ser Ser Gln Asn Gly Ala Glu Asp Thr Thr Asn Ser Gly Gly
145                 150                 155                 160 aaa agc agc cac agt gtg acc aca gac ctc aca tcc act aag gca gaa    528
Lys Ser Ser His Ser Val Thr Thr Asp Leu Thr Ser Thr Lys Ala Glu
                165                 170                 175 cat ctg acg acc cct cac cct aca agt cca ctt agc ccc cga caa ccc    576
His Leu Thr Thr Pro His Pro Thr Ser Pro Leu Ser Pro Arg Gln Pro
            180                 185                 190 act tcg acg cat cct gtg gcc acc cca aca agc tcg gga cat gac cat    624
Thr Ser Thr His Pro Val Ala Thr Pro Thr Ser Ser Gly His Asp His
        195                 200                 205 ctt atg aaa att tca agc agt tca agc act gtg gct atc cct ggc tac    672
Leu Met Lys Ile Ser Ser Ser Ser Ser Thr Val Ala Ile Pro Gly Tyr
    210                 215                 220 acc ttc aca agc ccg ggg atg acc acc acc cta ccg tca tcg gtt atc    720
Thr Phe Thr Ser Pro Gly Met Thr Thr Thr Leu Pro Ser Ser Val Ile
225                 230                 235                 240 tcg caa aga act caa cag acc tcc agt cag atg cca gcc agc tct acg    768
Ser Gln Arg Thr Gln Gln Thr Ser Ser Gln Met Pro Ala Ser Ser Thr
                245                 250                 255 gcc cct tcc tcc cag gag aca gtg cag ccc acg agc ccg gca acg gca    816
Ala Pro Ser Ser Gln Glu Thr Val Gln Pro Thr Ser Pro Ala Thr Ala
            260                 265                 270 ttg aga aca cct acc ctg cca gag acc atg agc tcc agc ccc aca gca    864
Leu Arg Thr Pro Thr Leu Pro Glu Thr Met Ser Ser Ser Pro Thr Ala
        275                 280                 285 gca tca act acc cac cga tac ccc aaa aca cct tct ccc act gtg gct    912
Ala Ser Thr Thr His Arg Tyr Pro Lys Thr Pro Ser Pro Thr Val Ala
    290                 295                 300 cat gag agt aac tgg gca aag tgt gag gat ctt gag aca cag aca cag    960
His Glu Ser Asn Trp Ala Lys Cys Glu Asp Leu Glu Thr Gln Thr Gln
305                 310                 315                 320 agt gag aag cag ctc gtc ctg aac ctc aca gga aac acc ctc tgt gca   1008
Ser Glu Lys Gln Leu Val Leu Asn Leu Thr Gly Asn Thr Leu Cys Ala
                325                 330                 335 ggg ggc gct tcg gat gag aaa ttg atc tca ctg ata tgc cga gca gtc   1056
Gly Gly Ala Ser Asp Glu Lys Leu Ile Ser Leu Ile Cys Arg Ala Val
            340                 345                 350 aaa gcc acc ttc aac ccg gcc caa gat aag tgc ggc ata cgg ctg gca   1104
Lys Ala Thr Phe Asn Pro Ala Gln Asp Lys Cys Gly Ile Arg Leu Ala
        355                 360                 365 tct gtt cca gga agt cag acc gtg gtc gtc aaa gaa atc act att cac   1152
Ser Val Pro Gly Ser Gln Thr Val Val Val Lys Glu Ile Thr Ile His
    370                 375                 380
```

```
act aag ctc cct gcc aag gat gtg tac gag cgg ctg aag gac aaa tgg      1200
Thr Lys Leu Pro Ala Lys Asp Val Tyr Glu Arg Leu Lys Asp Lys Trp
385                 390                 395                 400 gat gaa cta aag gag gca ggg gtc agt gac atg aag cta ggg gac cag      1248
Asp Glu Leu Lys Glu Ala Gly Val Ser Asp Met Lys Leu Gly Asp Gln
            405                 410                 415 ggg cca ccg gag gag gcc gag gac cgc ttc agc atg ccc ctc atc atc      1296
Gly Pro Pro Glu Glu Ala Glu Asp Arg Phe Ser Met Pro Leu Ile Ile
420                 425                 430 acc atc gtc tgc atg gca tca ttc ctg ctc ctc gtg gcg gcc ctc tat      1344
Thr Ile Val Cys Met Ala Ser Phe Leu Leu Leu Val Ala Ala Leu Tyr
        435                 440                 445 ggc tgc tgc cac cag cgc ctc tcc cag agg aag gac cag cag cgg cta      1392
Gly Cys Cys His Gln Arg Leu Ser Gln Arg Lys Asp Gln Gln Arg Leu
450                 455                 460 aca gag gag ctg cag aca gtg gag aat ggt tac cat gac aac cca aca      1440
Thr Glu Glu Leu Gln Thr Val Glu Asn Gly Tyr His Asp Asn Pro Thr
465                 470                 475                 480 ctg gaa gtg atg gag acc tct tct gag atg cag gag aag aag gtg gtc      1488
Leu Glu Val Met Glu Thr Ser Ser Glu Met Gln Glu Lys Lys Val Val
            485                 490                 495 agc ctc aac ggg gag ctg ggg gac agc tgg atc gtc cct ctg gac aac      1536
Ser Leu Asn Gly Glu Leu Gly Asp Ser Trp Ile Val Pro Leu Asp Asn
        500                 505                 510 ctg acc aag gac gac ctg gat gag gag gaa gac aca cac ctc tag          1581
Leu Thr Lys Asp Asp Leu Asp Glu Glu Glu Asp Thr His Leu
515                 520                 525

<210> SEQ ID NO 2
<211> LENGTH: 526
<212> TYPE: PRT
<213> ORGANISM: Homo sapiens

<400> SEQUENCE: 2

Met Arg Cys Ala Leu Ala Leu Ser Ala Leu Leu Leu Leu Leu Ser Thr
1               5                   10                  15

Pro Pro Leu Leu Pro Ser Ser Pro Ser Pro Ser Pro Ser Pro Ser Gln
                20                  25                  30

Asn Ala Thr Gln Thr Thr Thr Asp Ser Ser Asn Lys Thr Ala Pro Thr
            35                  40                  45

Pro Ala Ser Ser Val Thr Ile Met Ala Thr Asp Thr Ala Gln Gln Ser
        50                  55                  60

Thr Val Pro Thr Ser Lys Ala Asn Glu Ile Leu Ala Ser Val Lys Ala
65                  70                  75                  80

Thr Thr Leu Gly Val Ser Ser Asp Ser Pro Gly Thr Thr Leu Ala
                85                  90                  95

Gln Gln Val Ser Gly Pro Val Asn Thr Thr Val Ala Arg Gly Gly Gly
            100                 105                 110

Ser Gly Asn Pro Thr Thr Ile Glu Ser Pro Lys Ser Thr Lys Ser
        115                 120                 125

Ala Asp Thr Thr Thr Val Ala Thr Ser Thr Ala Thr Ala Lys Pro Asn
130                 135                 140

Thr Thr Ser Ser Gln Asn Gly Ala Glu Asp Thr Thr Asn Ser Gly Gly
145                 150                 155                 160

Lys Ser Ser His Ser Val Thr Thr Asp Leu Thr Ser Thr Lys Ala Glu
                165                 170                 175

His Leu Thr Thr Pro His Pro Thr Ser Pro Leu Ser Pro Arg Gln Pro
```

```
            180                 185                 190
Thr Ser Thr His Pro Val Ala Thr Pro Thr Ser Ser Gly His Asp His
        195                 200                 205
Leu Met Lys Ile Ser Ser Ser Ser Thr Val Ala Ile Pro Gly Tyr
        210                 215                 220
Thr Phe Thr Ser Pro Gly Met Thr Thr Thr Leu Pro Ser Ser Val Ile
225                 230                 235                 240
Ser Gln Arg Thr Gln Gln Thr Ser Ser Gln Met Pro Ala Ser Ser Thr
            245                 250                 255
Ala Pro Ser Ser Gln Glu Thr Val Gln Pro Thr Ser Pro Ala Thr Ala
            260                 265                 270
Leu Arg Thr Pro Thr Leu Pro Glu Thr Met Ser Ser Ser Pro Thr Ala
            275                 280                 285
Ala Ser Thr Thr His Arg Tyr Pro Lys Thr Pro Ser Pro Thr Val Ala
            290                 295                 300
His Glu Ser Asn Trp Ala Lys Cys Glu Asp Leu Glu Thr Gln Thr Gln
305                 310                 315                 320
Ser Glu Lys Gln Leu Val Leu Asn Leu Thr Gly Asn Thr Leu Cys Ala
            325                 330                 335
Gly Gly Ala Ser Asp Glu Lys Leu Ile Ser Leu Ile Cys Arg Ala Val
            340                 345                 350
Lys Ala Thr Phe Asn Pro Ala Gln Asp Lys Cys Gly Ile Arg Leu Ala
            355                 360                 365
Ser Val Pro Gly Ser Gln Thr Val Val Lys Glu Ile Thr Ile His
            370                 375                 380
Thr Lys Leu Pro Ala Lys Asp Val Tyr Glu Arg Leu Lys Asp Lys Trp
385                 390                 395                 400
Asp Glu Leu Lys Glu Ala Gly Val Ser Asp Met Lys Leu Gly Asp Gln
            405                 410                 415
Gly Pro Pro Glu Glu Ala Glu Asp Arg Phe Ser Met Pro Leu Ile Ile
            420                 425                 430
Thr Ile Val Cys Met Ala Ser Phe Leu Leu Leu Val Ala Ala Leu Tyr
            435                 440                 445
Gly Cys Cys His Gln Arg Leu Ser Gln Arg Lys Asp Gln Gln Arg Leu
            450                 455                 460
Thr Glu Glu Leu Gln Thr Val Glu Asn Gly Tyr His Asp Asn Pro Thr
465                 470                 475                 480
Leu Glu Val Met Glu Thr Ser Ser Glu Met Gln Glu Lys Lys Val Val
            485                 490                 495
Ser Leu Asn Gly Glu Leu Gly Asp Ser Trp Ile Val Pro Leu Asp Asn
            500                 505                 510
Leu Thr Lys Asp Asp Leu Asp Glu Glu Asp Thr His Leu
            515                 520                 525

<210> SEQ ID NO 3
<211> LENGTH: 10
<212> TYPE: PRT
<213> ORGANISM: Mus musculus
<220> FEATURE:
<221> NAME/KEY: SITE
<222> LOCATION: (1)..(10)

<400> SEQUENCE: 3

Ser Ala Ser Ser Val Ser Tyr Met His
1               5                   10
```

```
<210> SEQ ID NO 4
<211> LENGTH: 7
<212> TYPE: PRT
<213> ORGANISM: Mus musculus
<220> FEATURE:
<221> NAME/KEY: SITE
<222> LOCATION: (1)..(7)

<400> SEQUENCE: 4

Asp Thr Ser Lys Leu Ala Ser
1               5

<210> SEQ ID NO 5
<211> LENGTH: 9
<212> TYPE: PRT
<213> ORGANISM: Mus musculus
<220> FEATURE:
<221> NAME/KEY: SITE
<222> LOCATION: (1)..(9)

<400> SEQUENCE: 5

Leu Gln Trp Ser Ser Asn Pro Pro Thr
1               5

<210> SEQ ID NO 6
<211> LENGTH: 5
<212> TYPE: PRT
<213> ORGANISM: Mus musculus
<220> FEATURE:
<221> NAME/KEY: SITE
<222> LOCATION: (1)..(5)

<400> SEQUENCE: 6

Ser Tyr Val Met His
1               5

<210> SEQ ID NO 7
<211> LENGTH: 17
<212> TYPE: PRT
<213> ORGANISM: Mus musculus
<220> FEATURE:
<221> NAME/KEY: SITE
<222> LOCATION: (1)..(17)

<400> SEQUENCE: 7

Tyr Ile His Pro Tyr Asn Asp Gly Ile Lys Tyr Asn Glu Lys Phe Lys
1               5                   10                  15

Gly

<210> SEQ ID NO 8
<211> LENGTH: 8
<212> TYPE: PRT
<213> ORGANISM: Mus musculus
<220> FEATURE:
<221> NAME/KEY: SITE
<222> LOCATION: (1)..(8)

<400> SEQUENCE: 8

Ser Trp Asp Trp Tyr Phe Asp Val
1               5

<210> SEQ ID NO 9
<211> LENGTH: 380
<212> TYPE: DNA
<213> ORGANISM: Mus musculus
<220> FEATURE:
<221> NAME/KEY: V_region
```

<222> LOCATION: (1)..(378)

<400> SEQUENCE: 9

```
atg gat ttt caa gtg cag att ttc agc ttc ctg cta atc agt gcc tca        48
Met Asp Phe Gln Val Gln Ile Phe Ser Phe Leu Leu Ile Ser Ala Ser
1               5                   10                  15 gtc ata ata tcc aga gga caa att gtt ctc acc cag tct cca gca atc        96
Val Ile Ile Ser Arg Gly Gln Ile Val Leu Thr Gln Ser Pro Ala Ile
            20                  25                  30 atg tct gca tct cca ggg gag aag gtc tcc atg acc tgc agt gcc agc       144
Met Ser Ala Ser Pro Gly Glu Lys Val Ser Met Thr Cys Ser Ala Ser
        35                  40                  45 tca agt gta agt tac atg cac tgg tac cag cag aag tca ggc acc tcc       192
Ser Ser Val Ser Tyr Met His Trp Tyr Gln Gln Lys Ser Gly Thr Ser
    50                  55                  60 ccc aaa aga tgg att tat gac aca tcc aaa ctg gct tct gga gtc cct       240
Pro Lys Arg Trp Ile Tyr Asp Thr Ser Lys Leu Ala Ser Gly Val Pro
65                  70                  75                  80 gct cgc ttc agt ggc agt ggg tct ggg acc tct tac tct ctc aca atc       288
Ala Arg Phe Ser Gly Ser Gly Ser Gly Thr Ser Tyr Ser Leu Thr Ile
                85                  90                  95 agc agc atg gag gct gaa gat gct gcc act tat tac tgc ctg cag tgg       336
Ser Ser Met Glu Ala Glu Asp Ala Ala Thr Tyr Tyr Cys Leu Gln Trp
            100                 105                 110 agt agt aac cca ccc acg ttc gga ggg ggg acc aag ctg gaa at            380
Ser Ser Asn Pro Pro Thr Phe Gly Gly Gly Thr Lys Leu Glu
        115                 120                 125
```

<210> SEQ ID NO 10
<211> LENGTH: 126
<212> TYPE: PRT
<213> ORGANISM: Mus musculus

<400> SEQUENCE: 10

```
Met Asp Phe Gln Val Gln Ile Phe Ser Phe Leu Leu Ile Ser Ala Ser
1               5                   10                  15

Val Ile Ile Ser Arg Gly Gln Ile Val Leu Thr Gln Ser Pro Ala Ile
            20                  25                  30

Met Ser Ala Ser Pro Gly Glu Lys Val Ser Met Thr Cys Ser Ala Ser
        35                  40                  45

Ser Ser Val Ser Tyr Met His Trp Tyr Gln Gln Lys Ser Gly Thr Ser
    50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Leu Gln Trp
            100                 105                 110

Ser Ser Asn Pro Pro Thr Phe Gly Gly Gly Thr Lys Leu Glu
        115                 120                 125
```

<210> SEQ ID NO 11
<211> LENGTH: 409
<212> TYPE: DNA
<213> ORGANISM: Mus musculus
<220> FEATURE:
<221> NAME/KEY: V_region
<222> LOCATION: (1)..(408)

<400> SEQUENCE: 11

```
atg gaa tgg agt tgg ata ttt ctc ttt ctc ctg tca gga act gca ggt    48
Met Glu Trp Ser Trp Ile Phe Leu Phe Leu Leu Ser Gly Thr Ala Gly
 1               5                  10                  15 gtc cac tct gag gtc cag ctg cag cag tct gga cct gag ctg gta aag    96
Val His Ser Glu Val Gln Leu Gln Gln Ser Gly Pro Glu Leu Val Lys
             20                  25                  30 cct ggg gct tca gtg aag atg tcc tgc aag gct tct gga tac aca ttc   144
Pro Gly Ala Ser Val Lys Met Ser Cys Lys Ala Ser Gly Tyr Thr Phe
         35                  40                  45 act agc tat gtt atg cac tgg gtg aag cag aag cct ggg cag ggc ctt   192
Thr Ser Tyr Val Met His Trp Val Lys Gln Lys Pro Gly Gln Gly Leu
     50                  55                  60 gag tgg att gga tat att cat cct tac aat gat ggt att aag tac aat   240
Glu Trp Ile Gly Tyr Ile His Pro Tyr Asn Asp Gly Ile Lys Tyr Asn
 65                  70                  75                  80 gag aag ttc aaa ggc aag gcc aca ctg act tca gac aaa tcc tcc agc   288
Glu Lys Phe Lys Gly Lys Ala Thr Leu Thr Ser Asp Lys Ser Ser Ser
                 85                  90                  95 aca gcc tac atg gac ctc agc agc ctg acc tct gag gac tct gcg gtc   336
Thr Ala Tyr Met Asp Leu Ser Ser Leu Thr Ser Glu Asp Ser Ala Val
            100                 105                 110 tat tac tgt gca aga tcg tgg gac tgg tac ttc gat gtc tgg gcc gca   384
Tyr Tyr Cys Ala Arg Ser Trp Asp Trp Tyr Phe Asp Val Trp Ala Ala
        115                 120                 125 ggg acc acg gtc acc gtc tcc tca g                                  409
Gly Thr Thr Val Thr Val Ser Ser
    130                 135

<210> SEQ ID NO 12
<211> LENGTH: 136
<212> TYPE: PRT
<213> ORGANISM: Mus musculus

<400> SEQUENCE: 12

Met Glu Trp Ser Trp Ile Phe Leu Phe Leu Leu Ser Gly Thr Ala Gly
 1               5                  10                  15

Val His Ser Glu Val Gln Leu Gln Gln Ser Gly Pro Glu Leu Val Lys
             20                  25                  30

Pro Gly Ala Ser Val Lys Met Ser Cys Lys Ala Ser Gly Tyr Thr Phe
         35                  40                  45

Thr Ser Tyr Val Met His Trp Val Lys Gln Lys Pro Gly Gln Gly Leu
     50                  55                  60

Glu Trp Ile Gly Tyr Ile His Pro Tyr Asn Asp Gly Ile Lys Tyr Asn
 65                  70                  75                  80

Glu Lys Phe Lys Gly Lys Ala Thr Leu Thr Ser Asp Lys Ser Ser Ser
                 85                  90                  95

Thr Ala Tyr Met Asp Leu Ser Ser Leu Thr Ser Glu Asp Ser Ala Val
            100                 105                 110

Tyr Tyr Cys Ala Arg Ser Trp Asp Trp Tyr Phe Asp Val Trp Ala Ala
        115                 120                 125

Gly Thr Thr Val Thr Val Ser Ser
    130                 135

<210> SEQ ID NO 13
<211> LENGTH: 40
<212> TYPE: DNA
<213> ORGANISM: Artificial Sequence
<220> FEATURE:
<223> OTHER INFORMATION: Synthetic oligonucleotide primer
```

<400> SEQUENCE: 13
taatacgact cactataggg cgcgcagctg taaacggtag                               40

<210> SEQ ID NO 14
<211> LENGTH: 39
<212> TYPE: DNA
<213> ORGANISM: Artificial Sequence
<220> FEATURE:
<223> OTHER INFORMATION: Synthetic oligonucleotide primer

<400> SEQUENCE: 14
attaaccctc actaaaggga ggggtggac catcctcta                                 39

<210> SEQ ID NO 15
<211> LENGTH: 39
<212> TYPE: DNA
<213> ORGANISM: Artificial Sequence
<220> FEATURE:
<223> OTHER INFORMATION: Synthetic oligonucleotide primer

<400> SEQUENCE: 15
attaaccctc actaaaggga ggggtggac catcctcta                                 39

<210> SEQ ID NO 16
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 16
ccggaattca gaggcgacga cacgatgcg                                           29

<210> SEQ ID NO 17
<211> LENGTH: 38
<212> TYPE: DNA
<213> ORGANISM: Artificial Sequence
<220> FEATURE:
<223> OTHER INFORMATION: Synthetic oligonucleotide primer

<400> SEQUENCE: 17
ttttcctttt gcggccgcga ggtgtgtgtc ttcctcct                                 38

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 18
gtccacgagg tgctgcacaa t                                                   21

<210> SEQ ID NO 19
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 19
gtcactggct cagggaaata acc                                                 23

<210> SEQ ID NO 20
<211> LENGTH: 20

```
<212> TYPE: DNA
<213> ORGANISM: Artificial Sequence
<220> FEATURE:
<223> OTHER INFORMATION: Synthetic oligonucleotide primer

<400> SEQUENCE: 20
aagatggata cagttggtgc                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 21
tgtcaagagc ttcaacagga                                              20

<210> SEQ ID NO 22
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 22
ccggaattca gaggcgacga cacgatgcg                                    29

<210> SEQ ID NO 23
<211> LENGTH: 39
<212> TYPE: DNA
<213> ORGANISM: Artificial Sequence
<220> FEATURE:
<223> OTHER INFORMATION: Synthetic oligonucleotide primer

<400> SEQUENCE: 23
ttttcctttt gcggccgcga gaaggtgttt tggggtatc                         39

<210> SEQ ID NO 24
<211> LENGTH: 38
<212> TYPE: DNA
<213> ORGANISM: Artificial Sequence
<220> FEATURE:
<223> OTHER INFORMATION: Synthetic oligonucleotide primer

<400> SEQUENCE: 24
ttttcctttt gcggccgctg cccagttact ctcatgag                          38

<210> SEQ ID NO 25
<211> LENGTH: 39
<212> TYPE: DNA
<213> ORGANISM: Artificial Sequence
<220> FEATURE:
<223> OTHER INFORMATION: Synthetic oligonucleotide primer

<400> SEQUENCE: 25
ttttcctttt gcggccgcct gtgtctgtgt ctcaacatc                         39

<210> SEQ ID NO 26
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 26
```
ttttcctttt gcggccgctg tgaagttcag gacgagc    37

<210> SEQ ID NO 27
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 27
ttttcctttt gcggccgccg aagcgccccc tgcacag    37

<210> SEQ ID NO 28
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 28
ttttcctttt gcggccgctc ggcatatcag tgagatc    37

<210> SEQ ID NO 29
<211> LENGTH: 38
<212> TYPE: DNA
<213> ORGANISM: Artificial Sequence
<220> FEATURE:
<223> OTHER INFORMATION: Synthetic oligonucleotide primer

<400> SEQUENCE: 29
ttttcctttt gcggccgctt gggccgggtt gaaggtgg    38

<210> SEQ ID NO 30
<211> LENGTH: 38
<212> TYPE: DNA
<213> ORGANISM: Artificial Sequence
<220> FEATURE:
<223> OTHER INFORMATION: Synthetic oligonucleotide primer

<400> SEQUENCE: 30
ttttcctttt gcggccgcaa cagatgccag ccgtatgc    38

<210> SEQ ID NO 31
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 31
ttttcctttt gcggccgctt ctttgacgac cacggtc    37

<210> SEQ ID NO 32
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 32
ttttcctttt gcggccgcct tggcagggag cttagtg    37

<210> SEQ ID NO 33
<211> LENGTH: 37
<212> TYPE: DNA
<213> ORGANISM: Artificial Sequence

```
<220> FEATURE:
<223> OTHER INFORMATION: Synthetic oligonucleotide primer

<400> SEQUENCE: 33 ttttccttt  gcggccgccc  atttgtcctt  cagccgc                              37

<210> SEQ ID NO 34
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 34 ttttccttt  gcggccgcgt  cactgacccc  tgcctcc                              37

<210> SEQ ID NO 35
<211> LENGTH: 38
<212> TYPE: DNA
<213> ORGANISM: Artificial Sequence
<220> FEATURE:
<223> OTHER INFORMATION: Synthetic oligonucleotide primer

<400> SEQUENCE: 35 ttttccttt  gcggccgcct  ccggtggccc  ctggtccc                             38

<210> SEQ ID NO 36
<211> LENGTH: 38
<212> TYPE: DNA
<213> ORGANISM: Artificial Sequence
<220> FEATURE:
<223> OTHER INFORMATION: Synthetic oligonucleotide primer

<400> SEQUENCE: 36 ttttccttt  gcggccgcga  tgagggcat   gctgaagc                             38

<210> SEQ ID NO 37
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 37
taatacgact  cactataggg  cgcgcagctg  taaacggtag                          40

<210> SEQ ID NO 38
<211> LENGTH: 39
<212> TYPE: DNA
<213> ORGANISM: Artificial Sequence
<220> FEATURE:
<223> OTHER INFORMATION: Synthetic oligonucleotide primer

<400> SEQUENCE: 38
attaaccctc  actaaaggga  ggggtggac   catcctcta                           39
```